Figure 1:
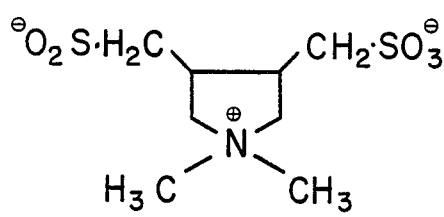
Figure 1:
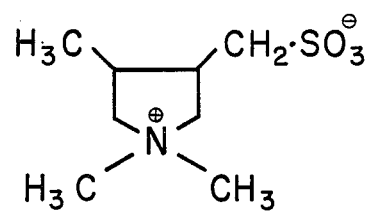
Figure 1:
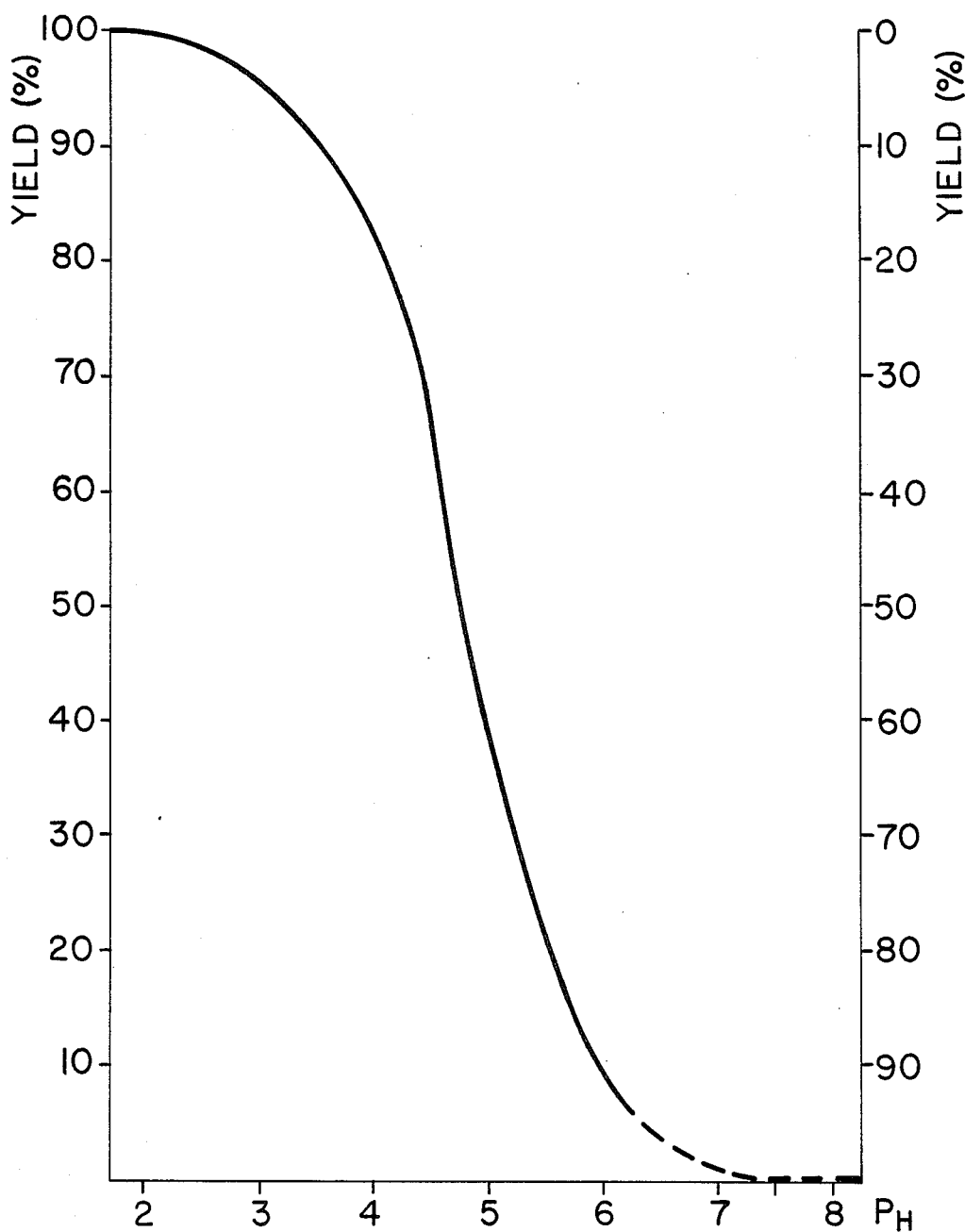

United States Patent [19]

Ballschuh et al.

[11] Patent Number: 4,877,885
[45] Date of Patent: Oct. 31, 1989

[54] NOVEL 3-SULFINATOMETHYL-OR 3-SULFONATOMETHYL-4-SULFOMETHYL PYRROLIDINIUM BETAINES AND THEIR SALTS AS WELL AS PROCESS FOR MAKING THE SAME

[75] Inventors: Detlef Ballschuh; Horst Seibt; Roland Ohme; Jochen Rusche; Egon Gruendemann; Elke Krause, all of Berlin, German Democratic Rep.

[73] Assignee: Akademie Der Wissenschaften Der DDR, Berlin, German Democratic Rep.

[21] Appl. No.: 35,254

[22] Filed: Apr. 2, 1987

Related U.S. Application Data

[63] Continuation of Ser. No. 748,156, Jun. 24, 1985, abandoned.

[30] Foreign Application Priority Data

Apr. 26, 1985 [DD] German Democratic Rep. ... 275642

[51] Int. Cl.$^4$ ............................................. C07D 209/96
[52] U.S. Cl. .................................. 548/570; 546/16; 548/409
[58] Field of Search ................... 548/570, 409; 546/16

[56] References Cited

U.S. PATENT DOCUMENTS 4,410,709 10/1983 Ohme et al. ..................... 548/570
4,528,383 7/1985 Schmitt ........................... 548/570 X

FOREIGN PATENT DOCUMENTS 0163319 12/1985 European Pat. Off. .
1173906 1/1965 Fed. Rep. of Germany .
02313539 1/1974 Fed. Rep. of Germany .
2331515 1/1974 Fed. Rep. of Germany .
2409412 8/1974 Fed. Rep. of Germany .
2007396 6/1983 German Democratic Rep. .

OTHER PUBLICATIONS

Z. Krebsforsch, 75, pp. 69–84 (1970), Druckrey et al.
Fernley; J. J. Am. Oil Chemist's Soc., Jan. 1978 (vol. 55), pp. 98–103.
Parris, et al.; J. Am. Oil Chemist's Soc., Feb. 1976 (vol. 53), pp. 60–63.
Linfield, et al.; J. Am. Oil Chemist's Soc., Jan. 1978 (vol. 55), pp. 87–92.
Parris, et al.; J. Am. Oil Chemist's Soc., Mar. 1976 (vol. 53), pp. 97–100.
Smith, et al.; J. Am. Oil Chemist's Soc., Oct. 1978 (vol. 55), pp. 741–744.

Primary Examiner—Joseph Paul Brust
Attorney, Agent, or Firm—Michael J. Striker

[57] ABSTRACT

Novel 3-sulfinatomethyl or 3-sulfonatomethyl-4-sulfomethyl-pyrrolidinium betaines are disclosed which have the formula

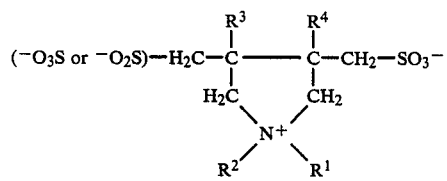

These novel compounds are obtained by reacting diallyl-triallyl ammonium salts or their methallyl derivatives with hydrogen sulfite in the presence of peroxo disulfates alone or in a mixture with other oxidation agents with a pH-value-range from 1.5 to 6.0 in a watery solution, whereby in light of the selection of the amount of hydrogen sulfite in combination with the amount peroxo disulfate different $SO_2^-$—or $SO_3^-$ substituted sulfomethyl-pyrralidinium betaines are generated.

The novel compounds are effective as specific tensides in a wide pH-range and can be extensively used as intermediary products.

7 Claims, 3 Drawing Sheets

NOVEL 3-SULFINATOMETHYL-OR 3-SULFONATOMETHYL-4-SULFOMETHYL PYRROLIDINIUM BETAINES AND THEIR SALTS AS WELL AS PROCESS FOR MAKING THE SAME

This application is a continuation application of Ser. No. 748,156, filed June 21, 1985, now abandoned.

The invention relates to novel 3-substituted 4-sulfomethyl pyrrolidinium betaines and their salts as well as a process for making the same.

Sulfobetaines are known wherein the cation is not a constituent of a ring system. These sulfobetaines are made preferably by alkylation of tertiary amines with derivatives of hydroxy alkan sulfonic acids (Parris, Weil, Linfield, J. Amer. Oil Chemists Soc. 53 (1976)97; DD-PS 139 719). However, mostly propansulton is used for introducing the sulfopropyl residue (DE-AS 24 31 031, 24 09 412). For example, Smith and Linfield (J. Amer. Oil Chemists Soc. 55 (1978) 741) obtained sulfobetaines with an additional sulfo group, which are characterized by a good lime soap dispersing characteristic, by reacting 2 Mol propansulton in hydroxy ethyl amino compounds. The grave disadvantage of this process consists, aside from its many steps, in that propansulton belongs to the most dangerous cancerogenics (Z. Krebsforschung, 75 (1970) 69; Registry of Toxic Effects of Chemical Substances, National Institute for Occupational Safety and Health, Maryland, USA, 1975 edition, 826) and can therefore be used for technical synthesises only when expensive health protective measures are applied.

Therefore, Linfield and his coworkers further suggest to deposit hydrogen sulfite on trialkylallyl ammonium salts (J. Amer. Oil Chemists Soc. 53 (1976) 60; 55 (1978) 87). The shortcoming of this process consists, on the one hand, in the operation without air as well as under pressure and, on the other hand, nonuniform reaction products are very frequently obtained during the long reaction times.

The deposition of buffered hydrogen sulfite solution on diallyl ammonium salts, like diethanol diallylammonium chloride is described in DE-PS 11 73 906. In accordance therewith, open chained double addition products, sulfobetaine sulfonates, are exclusively obtained.

The DE-OS 23 31 515 describes a process for a radical addition of hydrogen sulfite on nonsubstituted olefines, whereby the transitional metals of the 1st, 7th and 8th side group of the PSE are used as catalysts. However, the olefines suggested for this process are not comparable with the allyl ammmonium compounds of the invention, since they are nonsubstituted and have insulated double linkages. Therefore, they substantailly differ in their electron configuration and reactivity from the compounds used in accordance with the invention.

The making of sulfobetaines by avoiding the use of cancerogenic alkyls is made possible in accordance with U.S. Pat. No. 4,410,709 and DD-PS 2007 396, in that di-or triallyl ammonium compounds are reacted by a homogeneous catalytic operating radical hydrogen sulfite addition. In accordance with these processes sulfobetaines are accessible at a maximum with only one additional sulfopropyl group in the molecule.

It is an object of the subject invention to create a novel type of sulfobetaine sulfinate/-sulfonate by introducing one or a plurality of additional hydrophylic or hydrophylic and reactive acid residues in a sulfomethyl pyrrolidinium betaine without a forcible introduction of carbon containing substitutes, whereby these compounds should be made on the basis of good technical base products. This object is solved in accordance with the claim.

The novel 3-sulfinatomethyl- or 3-sulfonatomethyl-4-sulfomethyl-pyrrolidinium betaines have the formula I a and I b,

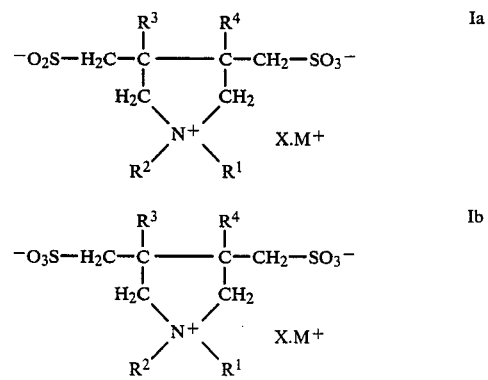

wherein
R¹ hydrogen, straight chained or branched alkyl with 1 to 22 C-atoms may be contained and in the chain —NH—CO— or —CO—NH—, whereby hydroxyalkyl, oxyalkylene, benzyl, represent;

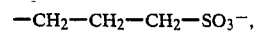
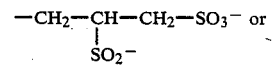
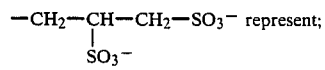

R² independent from R¹ hydrogen, straight chained or branched alkyl with 1 to 22 C-atoms, whereby in the chain —NH—CO— or —CO—NH— may be contained, hydroxyalkyl or oxyalkylene or together with R¹ signify a substitute closed into a ring, R³, R⁴ hydrogen or methyl M⁺ the same or different cationes, preferably of the sodium, potassium, ammonium or the hydrogen and wherein X represents a whole number from 1 to 3.

The subject matter of the invention is in furtherance a process for making the compounds of formula I a and I b. The novel compounds of formula I a and I b are obtained in accordance with the invention that diallyl ammonium salts of formula II

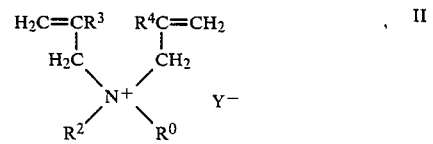

wherein R², R³ and R⁴ have the aforementioned significance, R⁰ independent from each other corresponds to the significance of R² and both together may also represent a substitute which is closed to a ring, and y⁻ is an anion or triallyl ammonium salts of the formula III,

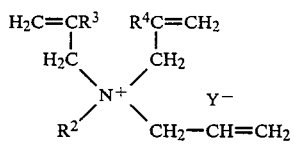

wherein $R^2$, $R^3$ and $R^4$ as well as y⁻ have the aforementioned significance, are reacted with molar amounts of a hydrogen sulfite in the presence of peroxo disulfates alone or in a mixture with other oxydation agents in the pH-range of 1.5 to 6.

Thereby the novel 3-sulfinatomethyl-4-sulfomethyl-pyrrolidinium betaines of the formula I a are generated in that diallyl compounds of the formula II are reacted with the double molar amount of the hydrogen sulfit in the presence of a catalytic amount of the peroxodisulfate at pH-values of 2 to 4. This reaction is called in the following a sulfocyclosulfination. The reaction occurs very quickly, the quantitative reaction is obtained in minutes or even seconds, and one obtains the end product in a very good purity, if in the mentioned pH-range a catalytic amount of a peroxodisulfate is added to the combined solvents of diallyl ammonium salt II and the hydrogen sulfite. The alkali or ammonium salts are preferably used as hydrogen sulfite.

The reaction is performed in accordance with the following equation:

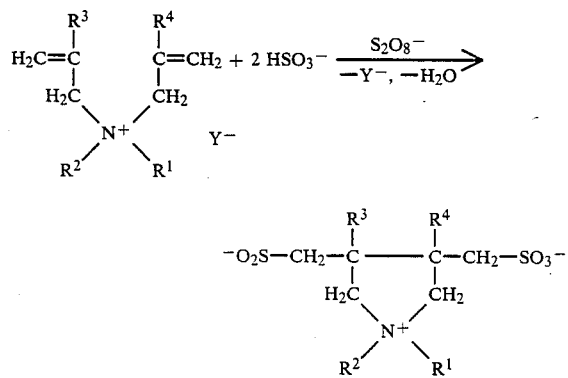

The formation of the sulfobetaine-sulfinates I a was also surprising because, as is known, sulfites can be easily converted into sulfates by the persulfate and therefore in accordance with the statements in the DE-OS 23 13 539 (page 4) must be considered as unsuitable initiator system in their combination.

The high reaction speed and the high selectivity with a quantitive reaction are totally surprising for a radical reaction initiated in a solution at room temperature. With the oxygen induced sulfocyclisation of the diallyl ammonium salts in the presence of transition metals one operates without from a large hydrogen sulfite excess in such a manner that the components are added drop by drop simultaneously over a long period of time to the reaction mixture, whereby the pH-value of the reaction mixture is in the upper buffer range of the hydrogen sulfite/sulfite system due to the given sulfite. These differences in the reaction conditions, in the pH-value, in the type of admixing of the reactants and the supply of sulfurous acid salts as well as the reaction initiations cause a completely different reaction process with respect to the known process in accordance with U.S. Pat. No. 4,410,709. The very short reaction times as well as the possibility of the simultaneous admixing of the components and the initiator enable a continous performance of the reaction, in that the simultaneous admixing is performed at the beginning of a dwell time path, for example, a tube reactor. Relative small reaction spaces may be used because of the very high space-time-yields of the inventive process during a discontinuous as well as a continuous reaction operation. Peroxodisulfates are used for initiating the sulfocyclosulfination, preferably in the range of 1 to 3 Mol-%; with a lower initiator amount an incomplete reaction will be achieved, while with a higher persulfate amount one obtains a further increase in the reaction speed but the danger of the uncontrollable violent reaction process (see example 12 as well as FIGS. 2 and 3) exists. An increase of the speed of the sulfocyclosulfination reaction is also achieved if the concentration of the base products is increased or if the initial temperature is increased, which, however, does not result in any practical advantages (see example 13). The initiating of the reaction is only successfully possible with peroxodisulfate; other per compounds, like hydrogen peroxide (see example 15) or perborat (see example 16) are not suitable for initiators, since they preferably oxydize sulfite into sulfate; air oxygen as an initiator can be principally used, but it results in longer reaction times and nonuniform products (see example 14). Above the optimum pH-value sulfobetaine is generated in an increased amount in addition to the sulfobetaine-sulfinate, which at pH-values over 5 finally results in the main product (see FIG. 1, table 1 and the examples 1 to 11). In special cases one could proceed in such a manner that the initiation is performed with a low amount of peroxodisulfate in the presence of transition metals (in a predetermined concentration range as in the process in accordance with U.S. Pat. No. 4,410,709) and that subsequently the reaction is continued with air oxygen to the complete reaction. However, in this mode of operation the formation of 3-methyl-4--sulfomethyl-pyrrolidinium-betain cannot be completely avoided, since during a prolonged reaction time a loss of sulfur dioxide occurs.

The obtained 3-sulfinatomethyl-4-sulfomethyl-pyrrolidinium betaines I a may be insulated from their reaction solution or may be further reacted as an intermediary product without insulation.

Furthermore, novel reactive 1-(3'-sulfo)propyl-3-sulfinatomethyl-4-sulfomethyl-pyrrolidinium betaines are obtained, if triallyl ammonium salts of the formula III with the triple molar amount of the hydrogen sulfite in the presence of a catalytic amount of the peroxodisulfate are reacted alone or in conjunction with a simultaneously or subsequently reaction of air oxygen at pH-values of 2.5 to 6.0, preferably 4.0 to 5.5. This trifunctionalisation of triallyl ammonium salts into products with three oxygen containing sulfur function should be designated as a sulfocyclosulfination. The exothermic reaction surprisingly triggered by this mode of process differs basically from all hitherto performed hydrogen sulfite additions on triallyl ammonium salts; the simultaneous building in of a sulfinate and two sulfonate groups represents a novel reaction. The speed of the reaction which is performed in accordance with a radical mechanism is also surprising; the sulfocyclosulfination requires only minutes with initiator concentrations <2 Mol-% or only seconds to a practically complete reaction when using concentrations of >2 Mol-%. Therefore, this reaction belongs to the fastest occuring radical reactions in solution which is known to the organic chemistry.

The triggering of the sulfocyclosulfination reaction is specifically bound to the presence of salts of the peroxo disulfuric acid, preferably sodium, potassium or ammonium peroxo disulfate; other per-compounds, for example, hydrogen peroxide or perborat, are not able to trigger a comparable reaction, but oxidize sulfite merely into sulfate.

In specific cases it is also possible to commonly use peroxo disulfates and other oxidation agents, for example, oxygen or in particular air in such a manner that about 1 Mol-% or less of a peroxo disulfate is added at the beginning phase for initiating the reaction while simultaneously stirring in air or passing through of air until the reaction is completed. However, with this mode of process longer reaction times have to be tolerated, however the composition of the reaction products does not change.

The selectivity of the reaction process is dependent to a high degree from the adjusted pH-value. In the preferred pH-value 4.0 to 5.5 the novel sulfobetaine sulfinates-sulfonates with a constituent of 50 to 70% are obtained in addition to the further sulfinated products 1-(2'-sulfinato-3'-sulfo)propyl-3-sulfinatomethyl-4-sulfomethyl-pyrrolidinium betaines A and the known (see DD-WP 200 739) 1-(3'-sulfo)propyl-3-methyl-4-sulfomethyl-pyrrolidinium betaines B.

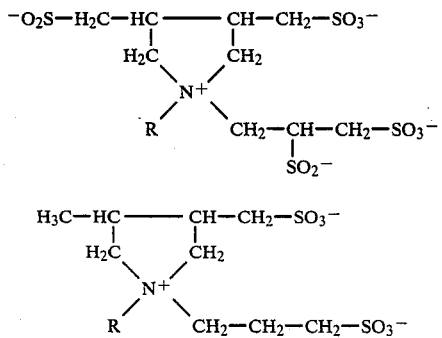

If the initial pH-value is lowered below 4, the reaction product practically does not contain B any longer, while with pH-values of 5.5 practically no A is formed. Therefore, the favorable pH-value range of 4.0 to 5.5 for performing the process is moreover achieved by mixing the triallyl ammonium salts with technical hydrogen sulfite solution, if need be, by adding low amounts of a base.

In accordance with the invention the triallyl ammonium salts III may be reacted with at least four times of the molar amount of the hydrogen sulfite in the presence of a catalytic amount of the peroxo disulfate with pH-values of 1.5 to 2.5.

The performance of the reaction in accordance with the invention is carried out in a simple manner in that 1 mol of a watery solution of a triallyl ammonium salts is converted with 4 mol of an alkali or ammonium hydrogen sulfite, adjust the pH-value of the reaction mixture from 1.5 to 2.5 and then adding all at once a catalytic amount of 1 to 4 Mol-% of an ammonium or alkali peroxo disulfate as a solid material or dissolved; starting at room temperature the exothermic reaction to the sulfinates is finished in about 1 to 3 minutes. The reaction is substantially quantitative, as can be determined by means of the sulfite consumption and the bromatometric product determination. $^1$H-NMR-spectroscopically one can recognize the completion of the reaction due to the disappearance of the allyl-proton signals. The limiting of the pH-value range from 1.5 to 2.5 in accordance with the invention is decisive for the selectivity, since with a higher pH-value the constituent of formed sulfonates is increased. Even with a careful exclusion of air oxygen, the reaction is initiated by peroxo disulfates, whereby their decisive role as initiators is documented. In special cases, a reaction which had been initiated by peroxo disulfate having a lack of peroxo disulfate (less than 0.5 Mol-%) can be continued with air oxygen, but only with a loss of selectivity and increase of reaction products without sulfinate groups.

In the specific case that the allyl ammonium salt used is a tertraallyl ammonium halide, one obtains the isomer spiro compounds IV in a double sulfocyclosulfination reaction which constitute bis-sulfobetaine sulfinate.

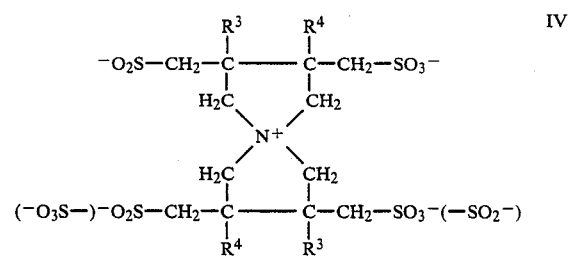

The novel 3-sulfonatomethyl-4-sulfomethyl-pyrrolidinium-betaines of the formula I b are generated in that diallyl ammonium salts of the formula II per Mol with the double molar amount of the hydrogen sulfite and the molar amount peroxo disulfate or with a simultaneous present of other oxydation agents are reacted with a total of two oxydation equivalents at pH-values of 2 to 4.

This reaction is performed in accordance with the following equation:

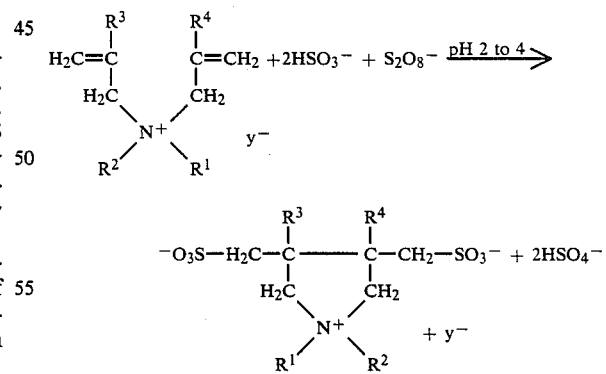

The reacton triggered by this mode of operation differs in its process and endproduct basically with respect to the corresponding 3-sulfomethyl-pyrrolidinium betains (U.S. Pat. No. 4,410,709) reaction with only 1 Mol hydrogen sulfite/mol diallyl ammonium salt and initiation with air oxygen/transition metal. The building in of a second sulfonic acid group under these conditions is surprising and was never determined in this form in other compound classes.

The reaction is specifically bound to the presence of peroxo disulfates. Other per-compounds, for example, hydrogen peroxide or alkali perborat do not trigger a comparable reaction, but merely oxidize sulfite into sulfate. However, it is possible, in accordance with the invention to use peroxo disulfates and other per-compounds together or to combine peroxo disulfates and other oxidation agents in such a manner that less than the molar quantity peroxo disulfate per mol Allyl compound is required. For this purpose the following agents are suitable, for example, hydrogen peroxide, chlor, chlorate bromate and many other more.

Preferably, one operates in accordance with the invention in such a manner that the diallyl ammonium salts are mixed in a watery solution with 2 mol hydrogen sulfite, adjust it to the pH-value 2 (to max. 4) and introduces the peroxo disulfate under stirring, whereby the progressive reaction is recognized by quick heating of the reaction mixture which can reach a boiling point.

Long chained substituted representatives result in pyrrolidinium betain sulfonates with tenside characteristics which precipitate from the reaction mixture and can be easily insulated and in a pure form. In other cases the generated sulfuric acid is neutralized before recovery and the betaine sulfonate is separated, if need be, extractively from the inorganic salt constituent.

The process in accordane with the invention may be continuously performed in a suitable device, if the components with the stated mol ratio are combined at the beginning of a dwell time path.

Furthermore, novel 1-(3'-sulfo)propyl-3,4-disulfomethyl-pyrrolidinium betaines are obtained, if triallyl ammonium salts of the formula III per Mol with the triple molar amount of the hydrogen sulfite and the molar amount peroxo disulfate or with a simultaneous presence of other oxidation agents are converted with a total of two oxidation equivalents at pH-values of 2.5 to 6.0, preferably between 4.0 and 5.5.

The exothermic reaction triggered by this mode of process also occurs quickly and sulfonizes the used triallyl ammonium salts quantitatevely in a few minutes. The selectivity of the reaction process is dependent to a high degree from the adjusted initial pH-value. In this manner, the novel sulfobetaine disulfonates are obtained in the pH-value from 4.0 to 5.5 with a constituent of 50 to 70% in addition to the four sulfonic acid groups containing 1-(2',3'-disulfo)propyl-3,4-disulfomethyl-pyrrolidinium betaines C and the known 1-(3'-sulfo)propyl-3-methyl-4-sulfomethyl-pyrrolidinium betaines B.

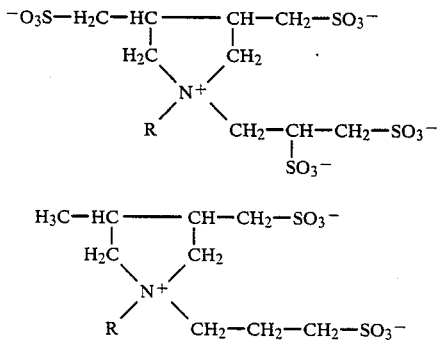

If the initial pH-value is lowered below 4, the reaction product does practically contain no compound B any longer, while at pH-values above 5.5 practically no compound C is formed. The pH-value range of 4.0 to 5.5 which is favorable for the performance of the process is moreover already achieved by mixing the triallyl ammonium salts with a technical hydrogen sulfite solution, if need be, by adding low amounts of soda lye.

The additional introduction of further sulfonic acid groups under the inventive conditions in compounds of the general formula B is completely surprising and was never observed in this form in other compound classes.

When making the sulfobetaine disulfonates one preferably operates in a watery solution with possible high concentrations of the reaction partners, in that the crystalline trially ammonium salts or their solutions are admixed with saturated technical hydrogen sulfite solution, adjust the pH-value of the mixture preferably between 4 and 5.5 and add the oxidation agent as a solution or in a crystalline form.

The progressive reaction is recognized by the very rapid heating of the reaction mixture. Thereby, the mixture can heat up to the boiling point, if the reaction partner are present in a high concentration. However, the strong exothermic reaction can be easily controlled, if the oxidation agent or the oxidation agent combination is added during a few minutes or by using outer cooling for discharging the released reaction heat.

Also, triallyl ammonium salts of the formula III per Mol also with the four times molar amount of the hydrogen sulfite and the double molar amount of the peroxo disulfate or at a simultaneous presence of other oxidation agents are reacted with a total of four oxidation equevalencies at pH-values of 1.5 to 2.5. Thereby, novel 1-(2',3'-disulfo)propyl-3,4-disulfomethyl-pyrrolidinium-betaines, which are sulfobotaines with 3 additional hydrophilic sulfonate groups are generated. In light of their charge carrying groups they may be used for making metal salts, as conductive salts or conductive coating agent. Compounds with such advantageous effects are hitherto not known.

Long chained substituted representatives of the novel compound class have good tenside characteristics in a wide pH-range.

The reaction triggered by the mode of process in accordance with the invention is carried out quickly, exothermic and quantitative and differs basically in its process and product from the sulfocyclisation in accordance with U.S. Pat. No. 4,410,709 of diallyl ammonium salts when initiating with air oxygen/transitional metal. The building in of 3 further sulfonic acid groups under the inventive conditions is surprising and was heretofore never observed in this form in other compound classes. All further facts correspond to the aforementioned described.

In particular the chloride, bromide, methosulfates or sulfates are suitable as di-and triallyl ammonium salts corresponding to the equivalent.

As further oxidations agents which are usable in the mixture with the peroxo disulfate chlor, or chlor emitting substances, chlorate, bromate, hydrogen peroxide or air, are preferably used as already described above.

The novel 3-sulfinatomethyl-4-sulfomethyl-pyrrolidinium betaines have valuable characteristics. Representatives with long chain substituents are useable as specific tensides.

In furtherance, these novel compounds also act as reactive intermediary products for other syntheses, since they have additional hydrophiles and polar groups: the sulfinate group which on account of its reactivity (nucleophil, alkylable, complex forming, reducing) makes the novel compounds useable for many interim products, and the sulfonate group which increases the polarity and solubility of the substances and defines the tenside characteristics of the substance group.

EXEMPLIFIED EMBODIMENTS

Examples 1 to 10 (see table 1/FIG. 1)

Sulfocyclosulfination of dimethyl diallyl ammonium chloride into pure sodium -1,1-dimethyl-3-sulfinatomethyl-4-sulfo-methyl-pyrrolidinium betaine ($R^1=R^2=CH_3$; $R^3=-CH_2-SO_2^-$; $R^4=R^5=H$ in the general formula I), sodium-1, 1-dimethyl-3-sulfinatomethyl-4-sulfomethyl-pyrrolidinium-betaine/1,1,3-trimethyl-4-sulfomethyl-pyrrolidinium betaine-mixtures and pure 1,1,3-trimethyl-4-sulfomethyl-pyrrolidinium betaine ($R^1=R^2=R^3=CH_3$; $R^4=R^5=H$ in the general formula I).

General operating instruction

For making pure sodium 1,1-dimethyl-3-sulfinatomethyl-4-sulfomethyl-pyrrolidinium betaine and their mixtures with 1,1,3-trimethyl -4-sulfomethyl-pyrrolidinium betaine:

307.4 g (1mol) 52.6% watery technical dimethyl diallyl ammonium chloride solution with 4.85% sodium chloride content, 516.5 g (2.02 mol) 40.7% technical sodium hydrogen sulfite solution with an iron content of 60 mg/l, the corresponding amount 37% hydrochloric acid or 33% soda lye for adjusting the given pH-value (see table 1) are successively introduced into a sulfonation flask provided with a stirrer, a thermometer and a glass electrode and as much water is added and homogenized so as to obtain an operating quantity of 1000 g, so as to assure the comparability of the obtained results.

In cases where larger amounts of soda lye are required for adjusting the pH-value, the base solution heats up. Before the reaction it should be cooled to room temperature. With the pale yellow initial solution which had been prepared in this manner one adds 5.4 g (2 Mol-%) finely powdered potassium peroxo disulfate under stirring, whereby the peroxodisulfate is immediately dissolved and the reaction solution assumes a blood red color in particular at pH-values under 5. With pH-values between 1.7 and 4.5 the reaction temperature increases within one minute (see table 1) by 45° to 50° C. The reaction is finished after reaching the maximum temperature.

With pH-values from 5 to 6.2 the reaction times extend to about 20 minutes. After the completed reaction one can decolor the red coloring of the reaction mixture which was caused by the use of iron containing chemicals by means of Fe-III-sulfinate by adding complex formers (for example, dimethyl amino methan bisphosphonic acid) or by setting a pH-value of about 7 which precipitates the dissolved iron salt as iron (III)-hydroxide and thereafter separate it from the colorless reaction mixture by filtration.

TABLE 1

Sulfocyclosulfination of dimethyl diallyl ammonium chloride under variation of the pH-value

| Example | pH-value | addition of 37% HCl (g) | addition of 33% NaOH (g) | reaction time up to the temperature maximum (min) |
|---|---|---|---|---|
| 1 | 1.7 | 60.0 | — | 1 |
| 2 | 2.0 | 35.0 | — | 1 |
| 3 | 2.5 | 12.8 | — | 1 |
| 4 | 3.0 | 5.5 | — | 1 |
| 5 | 4.0 | — | — | 1 |
| 6 | 4.5 | — | 4.50 | 1 |
| 7 | 5.0 | — | 7.6 | 2 |
| 8 | 5.5 | — | 20.0 | 4 |
| 9 | 6.0 | — | 42.7 | 15 |
| 10 | 6.2 | — | 121.2 | 20 |

An aliquote portion of the reaction solutions obtained in accordance with table 1 was reduced to a dry salt like residue and $^1$H-NMR-spectroscopically tested, whereby the quantititative composition is defined by comparing the intensities of suitable signals. The test results are compiled in FIG. 1. Accordingly, pure sulfobetaine sulfinates are accessible only after a pH-value $\leq 2$ (examples 1 and 2). The constituent of 1,1,3-trimethyl-4-sulfomethyl-pyrrolidinium betaine constantly increases with higher pH-values of the initial solution (examples 3 to 10).

An aliquote portion of the reaction solution made in accordance with example 2 (see table 1) was at first adjusted to the pH-value 7 by means of soda lye, mixed with a few drops $H_2O_2$ and after filtering off the insoluble iron (III)-hydroxide it was evaporated into a dry state under a reduced pressure. The remaining residue was $^{13}$C-NMR-spectroscopically tested ($D_2O$, external standard TMS). The spectrum showed that the sodium-1,1-dimethyl-3-sulfinatomethyl-4-sulfomethyl-pyrrolidinium betaine is present mainly in the cis-configuration with respect to the substitutes in the 3,4-position in addition to low trans-constituents.

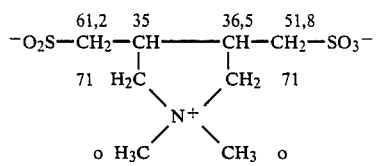

The numbers stated on the atom symbols correspond to the chemical displacements for the cis-configuration in ppm. o: 56.2;56.0;55.9/54,6;54,5;54,3. The N—CH$_3$-groups are not equivalent; signal splitting by $^{14}$N-quadrupol moment. The signals of the trans-compound at 38.6 ppm and 40.9 ppm correspond to the two CH-groups as well as at 63.9 ppm of the —CH$_2$-SO$_2^-$-group.

Example 11

Pure 1,1,3-trimethyl-4-sulfomethyl-pyrrolidinium betaine ($R^1=R^2=R^3=CH_3$; $R^4=R^5=H$ in the general formula I) by sulfocyclisation of dimethyl diallyl ammonium chloride at pH-values $\geq 7.5$ (see FIG. 1, dashed line)

18.8 g (0,15 mol) sodium sulfite in tap water were dissolved into a 125 ml solution in an open container being provided with a glass electrode and an intensive stirrer; the pH-value of the solution was 9.1. Under vigorous stirring air is finely distributed and stirred into the solution. Simultaneously and uniformly a solution of 46.1 g (0,15 mol) 52.6% dimethyl diallyl ammonium chloride solution, diluted with tap water to 50 ml and a solution of 38.35 g (0.15 mol) 40,7% technical sodium hydrogen sulfite solution, diluted with tap water to 50 ml are added dropwise from two burettes in such a manner that a pH-value of $\geq 7.5$ can be maintained. The dropwise adding of the two solutions requires 39 minutes; the reaction temperature increases during this time from 25° to 39° C. The pH-value remains between 7.65 and 8.0 during the dropwise adding phase. A $^1$H-NMR-spectrum prepared from the reaction solution and showed the quantitative reaction of the allyl ammonium salt to the sulfobetaine.

For testing the absence of sulfinate constituents see examples 1 to 10. The total reaction solution was reduced to a dry state under reduced pressure for separating the 1,1,3-trimethyl-4-sulfomethyl-pyrrolidinium betaine from the inorganic salts and the remaining crystalline residue was treated with concentrated hydrochloric acid. The hydrochloric acid solution was subsequently separated from the inorganic salts by filtration and was again reduced to a highly viscose stil hydrochloric containing syrup under a reduced pressure, from which the sulfobetaine started to crystallize in shining platelets after standing for a while. If some drops of an iron (III) sulfate-solution was added to a sample of the highly viscous which was dissolved in water the solution did not turn blood red which proves the absence of sulfinate constituents. By adding ethanol the betaine can be brought into crystallisation immediately, whereby a white crystal paste is generated. The sulfobetaine is not crystilliseable from water. Its $^{13}$C-NMR-spectrum resulted in chemical displacements for the individual C-atoms as already described in the DD-WP 154 444 (example 1a). For example, if the molar constituent of 1 Mol sodium sulfite is reduced to 0.6 Mol per mol dimethyl diallyl ammonium chloride and per mol sodium hydrogen sulfite one automatically reduces the buffer capacity of the reaction solution, whereby the duration of the dropwise adding increases from 39 minutes to 74 minutes, of a pH-value of 7.5 should be maintained. During a further reduction of the sodium sulfite-buffer only pH-values below 7.5 can be realized which enhances the forming of sulfobetaine sulfinate (see FIG. 1, dashed curved section).

Example 12

Figure 2:
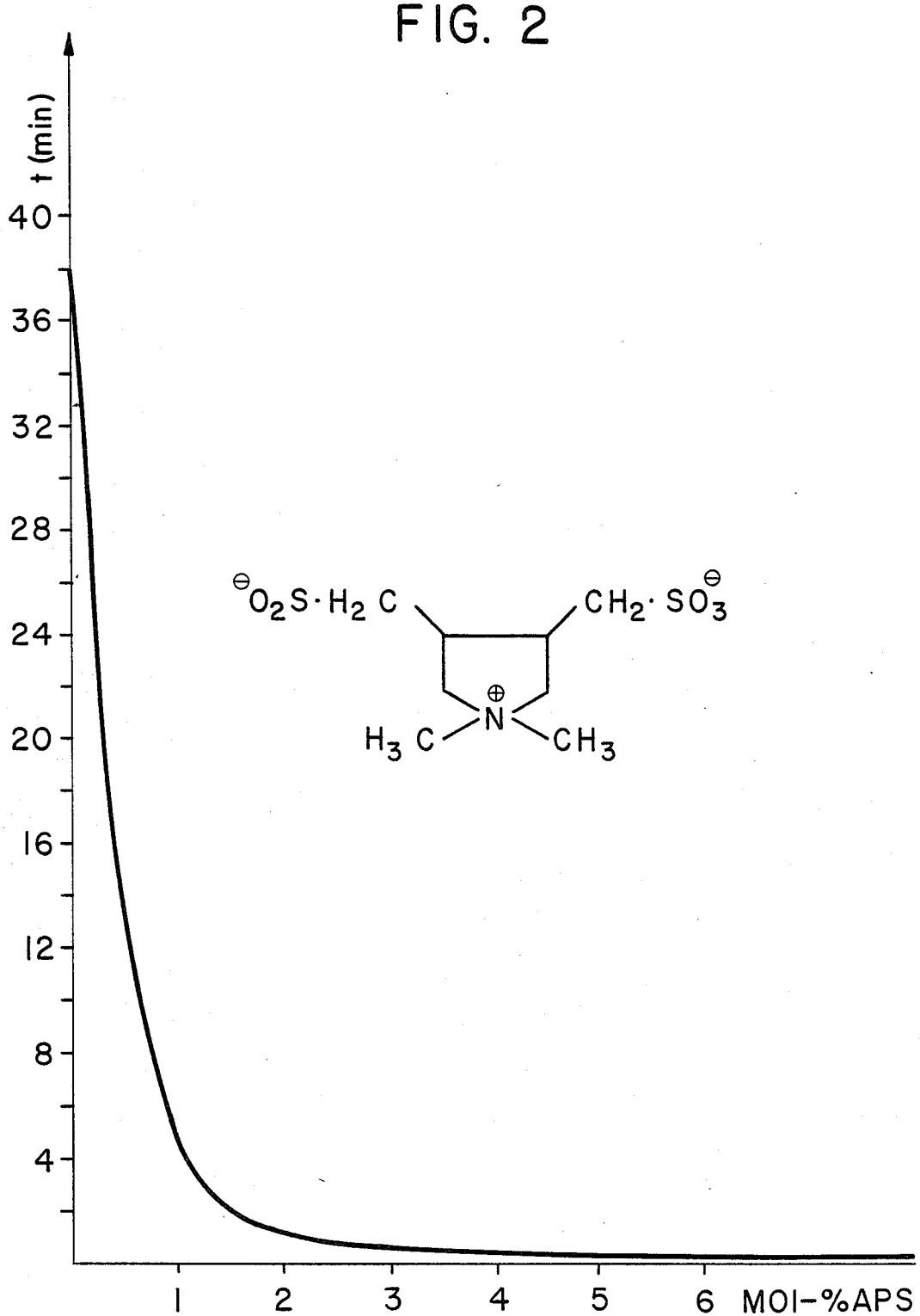

Sulfocyclosulfination of dimethyl diallyl ammonium chloride by variation of the initiator concentrations In this example the dependency of the duration of the exothermic sulfocyclosulfination reaction of the dimethyl diallyl ammonium chloride to the sodium-1,1-dimethyl-3-sulfinatomethyl-4-sulfomethyl-pyrrolidinium betaine ($R^1=R^2=CH_3$; $R^3=-CH_2-SO_2^-$; $R^4=R^5=H$ in the general formula I) from the used amount of ammonium peroxo disulfate (APS) at a pH-value of 2.5 and a concentration of 1 mol of the diallyl compound and 2.1 mol sodium hydrogen sulfite/kg reaction mixture should be illustrated (16.2% by weight dimethyl diallyl ammonium chloride). The initiator amount used is varied between 0 Mol-% and 8 Mol-% APS. The total result is illustrated in FIG. 2.

In a representative manner for the test series we would like to describe in detail the initiating with 4 Mol-% APS:

307.4 g (1 mol) 52,6% technical dimethyl diallyl ammonium chloride with 4.85% NaCl-content, 618.5 g (2,1 mol) 35.33% technical sodium hydrogen sulfite solution with a Fe$^{++}$-content of 8 mg/l and 12.8 g 37% hydrochloric acid were combined under stirring in a sulfonation flask provided with a stirrer and a thermometer. The pH-value was 2.5. Thereafter, 9.12 g (4 Mol-%) APS were dissolved in 52.2 g tap water and added to the prepared mixture under stirring. The reaction mixture colors immediately red and heats up after 10 seconds from 23° to 45° C.; after 15 seconds the temperature increases to 68° C. and after 20 seconds finally reaches the maximum of 71° C. At this point in time the reaction is quantitative. The reaction temperature is again dropped to 70° C. after one minute. The $^1$H-NMR-spectroscopic yield determination had a content of 98% sulfobetaine sulfinate in the reaction mixture (see example 3; FIG. 1). When initiating with still higher initiator concentrations, for example, 8 Mol-%, the reaction speed increases to such an extent that the reaction mixture vigorously boils within a few seconds immediately after the initiator is added.

Example 13

1,1-dimethyl-3-sulfinic acid methyl-4-sulfomethyl-pyrrolidinium betaine ($R^1=R^2=CH_3$; $R^3=-CH_2-SO_2H$; $R^4=R^5=H$ in the general formula I)

In a solution of a pH-value of two the following are admixed: 307.4 g (1 mol) 52,6% technical dimethyl diallyl ammonium chloride solution, 516.5 g (2.02 mol) 40.7% technical sodium hydrogen sulfite solution and 35 g 37% hydrochloric acid. Subsequently 5.4 g (2 Mol-%) finely powdered potassium peroxodisulfate are added under stirring. The solution color red immediately; after 30 seconds the temperature of the solution increases from 21° to 70.5° C. After this reaction time the reaction is already quantitative. (When using a still higher concentration of diallyl compound (for example 80%) the reaction speed becomes so high that the reaction mixtures violently boils immediately after adding the initiator (2 Mol-%).

For separating the sulfobetaine sulfinic acid from the inorganic salts, the cooled reaction solution is evaporated into a syrup like, salt like residue under a reduced pressure and is thoroughly processed with a sufficient amount of concentrated hydrochloric acid (500 g). Thereafter, mainly sodium chloride is filtered off from the inorganic salts and again evaporates the filtrate into a yellowish glazy mass from which a part of the sulfinic acid crystallizes after a short time. After intensive processing, by the addition of 500 ml ethanol, the complete crystallisation can be achieved. After suctioning off the ethanol as well as a two time afterwashIng with 250 ml ethanol each, suctioning off and drying up to the weight constant, finally 222 g powderlike, colorless, crystalline sulfinic acid is insulated with a constituent of 1.8% sodium chloride. The content of sulfinic acid was determined bromatometric to be 80%. The sulfinic acid starts to decompose at a temperature above 225° C. $^{13}$C-NMR-spectrum of the cis-sulfinic acid (D$_2$O, external standard TMS):

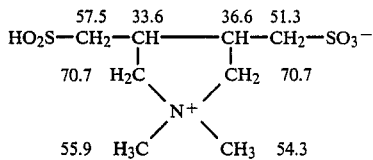

The numbers stated on the atom symbols correspond to the chemical displacements in ppm.

While a chemical displacement of 61.2 was determined for the sodium salt for group $NaO_2S-CH_2-$ (see example 2), the value for the sulfinic acid group was $HO_2S-CH_2-$ at 57.5 ppm.

By neutralising the sulfobetaine sulfinic acid with any given base, the given salts may be recovered pure of formula, if need be.

When the aforementioned test is repeated at an initial temperature of 0° C. one encounters a prolongation of the reaction time, but no reduction of the yield of sulfobetaine sulfinate. The time sequence of the exothermic sulfocyclosulfination is shown in the following summary:

| Time (min) | 0 | 1 | 2 | 2.5 | 3 | 3.3 | 5 |
|---|---|---|---|---|---|---|---|
| Temperature (°C.) | 0 | 1.5 | 3 | 25 | 41 | 50.5 | 50.3 |

The pale yellow reaction mixture changes to orange after 2 minutes and blood red after 2.5 minutes.

Example 14

This example and the two following should demonstrate the initiating of the sulfocyclosulfination of the dimethyl diallyl ammonium chloride with further initiators like oxygen, hydrogen peroxide and sodium perborate, as well their inferiority with respect to the inventive process.

(a) Sulfocyclosulfination by stirring in of air oxygen at a pH-value of 2.5.

One proceeds as described in example 12, but no ammonium peroxo disulfate is added, but one reacts 1 mol dimethyl diallyl ammonium chloride with 2.1 mol sodium hydrogen sulfite per kg reaction mixture at a pH-value of 2.5 under intensive stirring in of air. The solution heats in 38 minutes to a temperature of 56° C. (temperature maximum, see FIG. 2) starting with an initial temperature of 23° C., and gradually drops again under continued stirring. However, at the time of the temperature maximum no complete reaction is obtained; only after 2 hours no allyl ammonium salt can be shown $^1$H-NMR-spectroscopically.

(b) Sulfocyclosulfination by feeding air at a pH-value 4

23.05 kg (75 mol) 52.6% technical dimethyl diallyl ammonium chloride solution with 33,13 kg (112,5 mol) 35.33% technical sodium hydrogen sulfite solution were mixed in a 100 liter barrel. The pH-value of the solution was 4. Air was fed through the solution under vigorous stirring in such a manner that air bubbles were finely dispersed therein.

The excess air which pearls through the reaction mixture was heavily enriched with sulfur dioxide and was fed into an exhaust. The time sequence of the exothermic sulfocyclosulfination is shown in the following summary:

| Time (min) | 0 | 10 | 20 | 30 | 40 | 45 | 50 | 60 | 120 |
|---|---|---|---|---|---|---|---|---|---|
| Temperature (°C.) | 15 | 28 | 37 | 63 | 84 | 86 | 85.5 | 84 | 73 |

The sediment did not contain any allyl ammonium salt any longer after 2 hours, while sulfite could still be shown iodometrically. The analytical test of the reaction product did show that the sulfobetaine sulfinate was only present in a yield of about 35% in addition to sulfobetain. During the analog reaction with the pH-value 4 as well as initiating with potassium peroxo disulfate, the sulfobetaine sulfinate could be obtained in a much higher yield at a shorter reaction time (see FIG. 1 as well as example 5 in table 1).

Example 15

Sulfocyclosulfination of dimethyl diallyl ammonium chloride with $H_2O_2$

One proceeds as described in example 12, however instead of ammonium peroxo disulfate 2 Mol-% 30% hydrogen peroxide is added to the reaction mixture. Thereafter, the temperature did rise by 2° C. within 15 seconds. A further temperature increase was not observed. The temperature only increased after a 2 hour stirring in of air (analog example 14a), that is, the reaction was completed only after the effect by the air.

Example 16

Sulfocyclosulfination of dimethyl diallyl ammonium chloride with sodium perborate One proceeds as described in example 15, however instead of hydrogen peroxide 2 Mol-% sodium perborate was added to the reaction mixture. The reaction temperature also increased by 2.5° C. in only 30 seconds. Only nonreacted base material could be shown in the reaction product.

Example 17

Sulfocyclosulfination of dimethyl-di-2-methallyl ammonium chloride

One proceeds as described in example 12 and reacts the combined solutions of 73 g of a total substance of 5.32 g (30 mmol) dimethyl-di-2-methallyl ammonium chloride/$^{13}$C-NMR-spectrum in ppm: 134.9 (C); 129.1 ($CH_2=$); 72.2 ($-CH_2-$); 518; 51.6; 51.5 ($N-CH_3$); 25.0 ($C-CH_3$)/; 65 mmol sodium hydrogen sulfite, hydrochloric acid, tap water and 5 Mol-% sodium peroxo disulfate at a pH-value of 2.1. The reacting mixture heats from 22° C. to 33° C. during the course of the reaction.

The $^{13}$C-NMR-spectrum of the obtained neutralized reaction product did show that it was not a uniform product—cis/transisomeres of 1,1,3,4-tetramethyl-3-sulfinatomethyl-4-sulfomethyl-pyrrolidinium betaine

```
            21.8   x        19.6   x
            H3C              CH3
     o  60.6  |           |  47.9   x
  -O2S—H2C—C————————C—CH2—SO3-
         48.8 |           | 49.9
       74.4 H2C           CH2  74.4
              \          /
               \   N+   /
              /        \
          H3C            CH3
            57.5/56.5
```

-continued x;0: signals may be reversed and
1,1,3,3,4-pentamethyl-4-sulfomethyl-pyrrolidinium-betaine

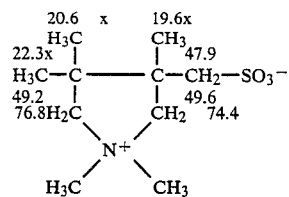

o 60.6;60.5;60.3;60;1
x;o: signal may also be reversed

The chemical displacements are only stated for the cis-compounds. The N—CH$_3$-groups are not equivalent.

Example 18

Sodium-1-methyl-3-sulfinatomethyl-4-sulfomethyl-pyrrolidinium betaine ($R^1=R^4=R^5=H$; $R^2=CH_3$; $R^3=-CH_2-SO_2^-$ in the general formula I) by sulfocyclosulfination of methyldiallyl amine hydrochloride One proceeds as in example 12 and reacts with 2 Mol-% potassium peroxo disulfate in an operating amount of 1 kg at a pH-value of 2 exactly 1 Mol methyl diallyl amine hydrochloride and 2,02 mol sodium hydrogen sulfite. The reaction product obtained showed the following $^{13}$C-NMR-spectrum (D$_2$O, external standard TMS)

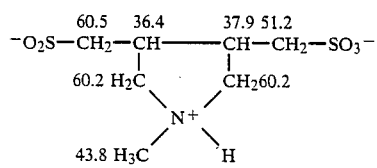

The numbers stated on the C-atom symbols correspond to the chemical displacements for the cis-configuration in ppm. If the free sulfinic acid should be isolated, one can separate the same from the organic salts in the mode or the process described in example 13. By neutralisation of the sulfinic acid with one or two mol equivalents of a given base the given salts, the sulfobetaine sulfinates or the 1-methyl-pyrrolidin-3-sulfinate-4-sulfonates can be recovered formula pure.

Example 19

Sodium-3-sulfinatomethyl-4-sulfomethyl-pyrrolidinium betaine ($R^1=R^2=R^4=R^5=H$; $R^3=CH_2-SO_2^-$ in the general formula I)

One proceeds in accordance with example 12 and reacts with 2 Mol-% potassium peroxo disulfate in an operating amount of 1 kg at a pH-value of 2 exactly 1 mol diallylamine hydrochloride and 2.02 mol sodium hydrogen sulfite. $^{13}$C-NMR-spectrum of the reaction product (D$_2$O, external standard TMS):

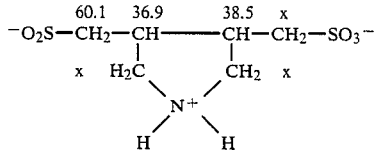

The statements of numbers on the C-atom symbols correspond to the chemical displacements for the cis-configuration in ppm. x: 49.7;50.2;50.5.

If the free sulfonic acid should be isolated, one can separate them from the inorganic salts in the mode of process described in example 13.

By neutralizing the sulfinic acid with given base, the given salts, the sulfobetaine sulfinates or the pyrrolidin-3-sulfinate-4-sulfonates can be recovered formula pure.

Example 20

3-methyl-4-sulfomethyl-pyrrolidinium betaine ($R^1=R^2=R^4=R^5=H$; $R^3=CH_3$ in the general formula I) by sulfocyclisation of diallyl amine hydrochloride One proceeds in accordance with the mode of process described in example 11, in that with a pH-value $\geq 7.5$ diallyl amine hydrochloride with buffered sodium hydrogen sulfite solution are reacted. $^{13}$C-NMR-spectrum of the reaction product (D$_2$O, external standard TMS):

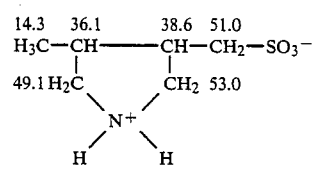

The statements of the numbers on the C-atom symbols correspond to the chemical displacements for the cis-configuration in ppm.

Example 21

Sodium-1-benzyl-1-methyl-3-sulfinatomethyl-4-sulfomethyl-pyrrolidinium betaine ($R^1=CH_2-C_6H_5$; $R^2=CH_3$; $R^3=-CH_2-SO^-_2$; $R^4=R^5=H$ in the general formula I) by sulfocyclosulfination of benzyl methyl diallyl ammonium chloride One proceeds as in example 12 and reacts with 2 Mol-% sodium peroxo disulfate in an operating amount of 1 kg at a pH-value of 2 exactly 1 mol benzyl methyl diallylammonium chloride and 2.02 mol sodium hydrogen sulfite.

$^{13}$C-NMR-spectrum of the cis-reaction product (statements as above):

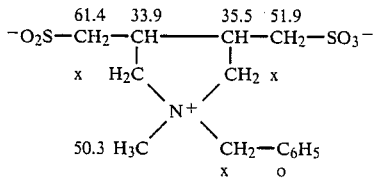

x: 68.5; 68.8; 70.2;
o: 129.6; 130.9; 132.4; 134.1

The free sulfinic acid can be recovered pure when operating in the mode of process described in example 13.

Examples 22 and 23

Sodium-1-fatty alkyl-1-methyl-3-sulfinatomethyl-4-sulfomethyl-pyrrolidinium betaine ($R^1$=fatty alkyl; $R^2$=$CH_3$; $R^3$=—$CH_2$—$SO_2^-$; $R^4$=$R^5$=H in the general formula I) by sulfocyclosulfination of methyl fatty alkyl diallyl ammonium bromide

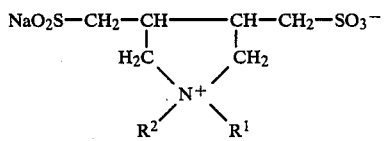

TABLE 2

Sodium-1-fatty alkyl-1-methyl-3-sulfinatomethyl-4-sulfomethyl-pyrrolidinium betaines

| Example | $R^1$ | $R^2$ | Melting point (°C.) |
|---|---|---|---|
| 22 | n-$C_{12}H_{25}$ | $CH_3$ | Decomposition 226° C. |
| 23 | n-$C_{16}H_{33}$ | $CH_3$ | 196° C. (decomposition as sulfinic acid) |

1 mol of the crystalline methyl fatty alkyl diallyl ammonium bromide is dissolved in 2.1 mol of a 40.7% technical sodium hydrogen sulfite solution; in the case of the hexadecyl ammonium salt the bisulfite solution must be heated to about 40° C., so that the salt dissolves. Subsequently, the pH-value of the solutions is adjusted to 2 with concentrated hydrochloric acid and the reaction is initiated by adding of 2 Mol-% of a 50% ammonium peroxo disulfite solution. The reacting solutions assume a red color immediately after the adding of the initiator and reach a maximum reaction temperature after 50 seconds. While the dodecyl sulfinate remains dissolved, the hexadecyl sulfinate starts to crystallize from the cooling solution. The separation of the pure sulfinates from the inorganic salts may also be performed by extracting the evaporated reaction solution with ethanol.

Also, the recovery of the free sulfinic acids may be performed in accordance with the process described in example 13.

The given salts may be recovered formula pure by neutralizing the sulfinic acids with given base.

Example 24

Sodium-1-dodecyl/tetradecyl amino carbonyl methyl-1-methyl-3-sulfinatomethyl-4-sulfomethyl-pyrrolidinium betaine
($R^1$=$CH_2$CO—NH—$C_{12}H_{25}$/$C_{14}H_{29}$; $R^2$=$CH_3$; $R^3$=—$CH_2$—$SO_2^-$; $R^4$=$R^5$=H in the general formula I)

Sulfocyclosulfination of N,N-diallyl-N-methyl-ammonio-acetic acid-dodecyl/tetradecyl amide-chloride under variation of the initiator concentration:

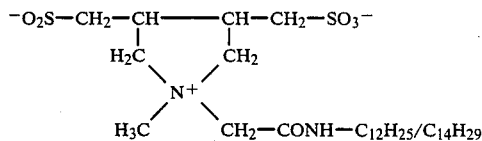

(a) synthesis of the base product

N,N-diallyl-N-methyl-ammonio-acetic acid methyl ester-chloride. 1112 g (10 mol) methyl diallyl amine are placed into a stirring container. 1085 g (10 mol) chlor acetic acid methyl ester is added drop by drop at an initial temperature of 35° C. The temperature increases to 70° C. during the drop by drop addition and must be kept at a range of from 70° to 80° C. either by regulating the drop by drop speed or by an occasional cooling. A complete reaction is obtained after about 30 minutes and a clear transparent very viscous liquid is obtained.

(b) N,N-diallyl-N-methyl ammonio-acetic acid-dodecyl/tetradecyl amide chloride 1990 g (10 mol) dodecyl/tetradecyl amine-mixture (coconut amines, component ratio 1:1) are added drop by drop to the aforedescribed methyl esteer chloride within 30 minutes, so that the raction temperature does not exceed 80° C. The highly viscous end product had a pH-value of 7.

The dependency of the duration of the exothermic sulfocyclosulfination of 1 mol of the aforementioned described amide-chloride with 2:1 mol sodium hydrogen sulfite in 1,1 kg reaction mixture with a pH-value of 2.2 was tested in a test series (see example 12).

Figure 3:
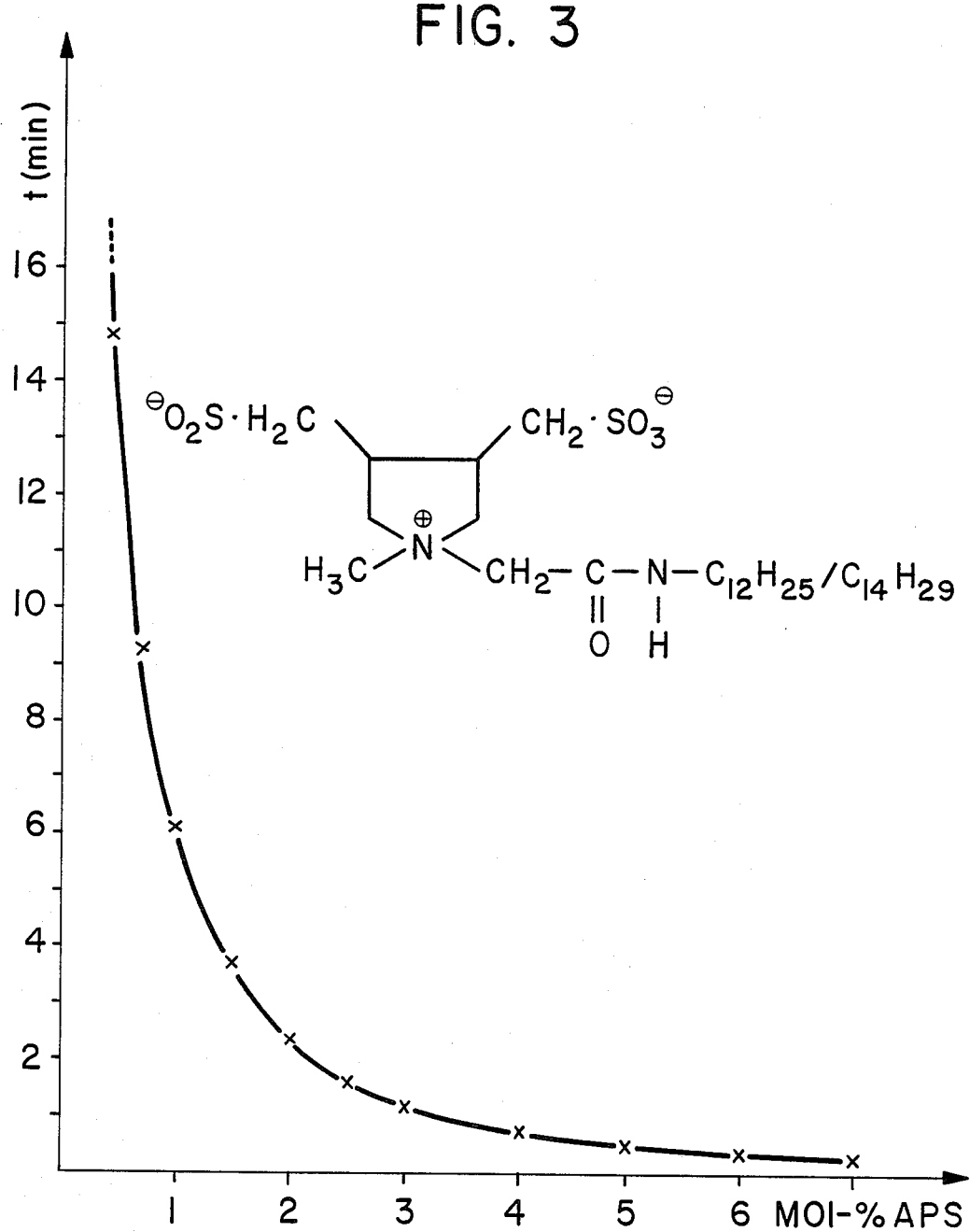

The initiator amount used was varied between 0 and 7 Mol-% ammonium peroxo disulfate. The given initial temperature was 40° C. The total result is illustrated in FIG. 3. With initiator amounts below 0.5 Mol-% none or only low degrees of reaction were obtained, while in amounts above 7 Mol-% the reaction mixture vigorously boils within a few seconds immediately after the addition of the initiator.

The time sequence of the exothermic sulfocyclosulfination by initiating with 2 Mol-% ammonium peroxo disulfate is shown in the following summary:

| Time (s) | 0 | 5 | 15 | 25 | 35 | 100 | 140 | 150 | 170 |
|---|---|---|---|---|---|---|---|---|---|
| Temperature (°C.) | 40 | 48 | 63 | 67 | 71 | 75 | 78 | 78 | 76 |

The initially pale yellow suspension assumes an orange color shortly after the initiator is added, it becomes homogenic and appears milky white when the air bubbles are stirred in. The cooled reaction solution represents a homogenic clear transparent solution of a pale yellow color. When diluting a sample with water the larger part of the generated sulfobetaine sulfinate precipitates. The generated suspension foams vigorously during shaking. The separation of the pure sulfobetaine sulfinic acid from Schmp. 219° C. (decomposition) from the inorganic salts may be performed by extraction of the evaporated acid solution.

Examples 25 to 27

Sodium-1-alkyl amino carbonyl methyl-1-methyl-3-sulfinatomethyl-4-sulfomethyl-pyrrolidium betaines ($R^1=CH_3$; $R^2=CH_2-CO-$alkyl amide; $R^3=CH_2-SO^-$; $R^4=R^5=H$ in the general formula I)

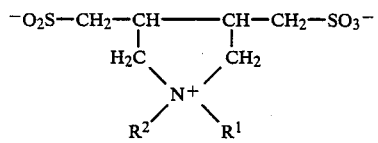

The manufacturing of the initial products of the N,N-diallyl-N-methyl-ammonio-acetic acid-alkyl amide-chlorides is performed in the mode of the process described in example 24. The sulfocyclosulfination into the sulfobetaine sulfinates is performed in accordance with example 22 and 23.

The reaction products obtained are characterized in table 3.

TABLE 3

Sodium-1-alkyl amino carbonyl methyl-1-methyl-3-sulfinatomethyl-4-sulfomethyl-pyrrolidinium betaines

| Example | $R^1$ | $R^2$ $-CH_2-CO-$alkyl amide | Melting point (°C.) |
|---|---|---|---|
| 25 | $CH_3$ | $-CH_2-CONH-C_4H_9$ | decomposition 264° C. |
| 26 | $CH_3$ | $-CH_2-CONH-C_6H_{13}$ | 168° C. (decomposition as sulfinic acid) |
| 27 | $CH_3$ | $-CH_2-CONH-C_8H_{17}$ | decomposition 218° C. |

Example 28

Sodium-1-/di-(dodecyl/tetradecyl-amino carbonyl)/methyl-1-methyl-3-sulfinatomethyl-4-sulfomethyl-pyrrolidinium betaine ($R^1=CH(CONH-C_{12}H_{25}/C_{14}H_{29})_2$; $R^2=CH_3$; $R^3=-CH_2-SO_2^-$; $R^4=R^5=H$ in the general formula I) by sulfocyclosulfination of N,N-diallyl-N-methyl-ammonio-malonic acid-didodecyl/tetradecyl amide-bromide

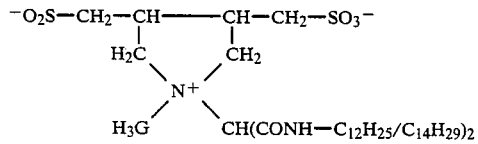

N,N-diallyl-N-methyl-ammonio-malonic acid-di-dodecyl/tetradecylamide-bromide 111 g (1 mol) methyl diallyl amine are dissolved in 200 ml ethanol. 239 g (1 mol) brome malonic acid diethyl ester is added drop by drop to this solution under stirring at 40° C. and therafter heated to 80° C. for 2 hours. Subsequently, 398 g (2 mol) dodecyl/tetradecyl amine-mixture (cocosamine, component ratio (1:1) is gradually added to this solution. The solution is heated for another 4 hours at 80° C. for completing the reaction. About half of the solvent is removed in a vacuum at 40° C.

Sodium-1-/di-(dodecyl/tetra decyl amino-carbonyl)/methyl-1-methyl-3-sulfinatomethyl-4-sulfomethyl-pyrrolidinium betaine The remaining raw product is diluted with 400 ml water; 630 g of a 40.7% sodium hydrogen sulfite solution are added to the solution. A pH-value of 2.0 is adjusted with concentrated hydrochloric acid. The mixture is subsequently heated to 50° C. A yellowish turbid solution is obtained when reaching this temperature which is subsequently reacted with 5.7 g (2.5 Mol-%) ammonium peroxo disulfate. Thereby, the temperature increases to 82° C. The generated sulfo betaine sulfinate precipitates during cooling. It is separated and recrystallized from ethanol (Mp. melting point 78° C.).

Example 29

Sodium-1.1-dimethyl-3.4-disulfomethyl-pyrrolidinium betaine ($R^1=R^2=CH_3$; $R^3=-CH_2-SO^-$; $R^4=R^5=H$ in the general formula I) from dimethyl diallyl ammonium chloride 349.2 g (1 mol) 46.3% technical dimethyl diallyl ammonium chloride solution, 533.6 g (2 mol) 39% technical sodium hydrogen sulfite solution with an iron content of 9 mg/mol solution as well as 30 g 37% hydrochloric acid ar admixed to a homogenic solution of a pH-value of 2.1 in a sulfonation flask which is provided with a stirrer, a returnflow coller, drop funnel and a thermometer. A 40% watery sodium peroxo disulfate solution, which had been prepared from 238.1 g (1 mol) sodium peroxo disulfate and 357.15 water is added to the prepared initial pale yellow initial solution to such a degree that the reacting solution heats to a boiling in about a minute starting at room temperature. During this time the solution is colored red. The dosaging of the persulfate solution is efficiently continued, so that the reaction heat of the solution, which starts to boil at 103° C., can be easily discharged by means of boiling cooling which requires about 5 minutes.

After about three quarters of the peroxo disulfate solution had been added, the reaction solution increasingly became clear and at the end it was yellow-green. A $^1H$-NMR-spectrum which had been prepared from the solution is acknowledged the quantitative and selective reaction of the diallyl ammonium salt into the sulfobetaine sulfonate. After the neutralisation of the solution with a 33% soda lye, the iron salts which were contained in the solution due the use of technical chemicals flocculates as an iron III-hydroxide and could be filtered out from the larges portion of the crystalline sodium sulfate. A $^{13}C$-NMR-spectrum which had been prepared from the colorless filtrate did show that the sulfobetaine sulfonate is mainly present in the cis-configuration in addition to low trans-constituents.

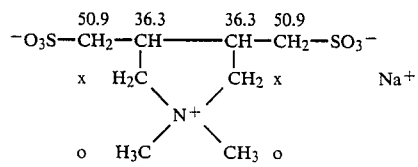

x: 70.8; 70.7; 70.5. Signal splitting by $^{14}N$-quadrupole moment o: 56.1; 55.9; 55.7/54.5; 54.3; 54.1.

The N—$CH_3$ groups are not equivalent; signal splitting by $^{14}N$-quadrupole moment.

trans-compound: 70.2 (N-CH$_2$); 53.7 (N-CH$_3$); 40.2 (CH).

If the sulfobetaine sulfonate should be completely separated from its inorganic accompanying salts and should the free 1,1-dimethyl-3-sulfonic acid methyl-4-sulfomethyl-pyrrolidinum betaine be isolated, one could proceed as follows: After reducing the aforementioned recovered reaction solution into a dry stage, one reacts the obtained salt residue with a sufficient amount of concentrated hydrochloric acid and process it very well, filters it off from the undissolved sodium salts and evaporates the hydrochloric acid solution of the sulfobetaine sulfonic acid under a reduced pressure into a dry state. Shortly thereafter the sulfonic acid starts to crystallize; adding of ethanol a complete crystallisation can be achieved. The colorless crystalline sulfobetaine sulfonic acid, which decomposes from 220° C., can be isolated by suctioning off the ethanol and drying the crystal paste. The $^{13}$C-NMR-spectrum of this acid is completely identical with the one of the corresponding sodium salt. The sodium betaine sulfonate may be recovered pure and in a crystalline form by again dissolving the sulfonic acid in the equimolar amount soda lye and reducing the obtained solution. The given salts may be recovered formula pure, if need be, by neutalisation of the sulfobetaine sulfonic acid with a given base.

Example 30

This example should demonstrate the influence of the initial-pH-value with respect to the selectivity of the reaction in process.

One proceed as described in detail in example 29 and mixes 69.84 g (0.2 mol) 46.3% dimethyl diallyl ammonium chloride solution with 106.7 g (0.2 mol) 39% sodium hydrogen sulfite solution into a homogenic solution, whose pH-value was 4.1. 119.05 g (0.2 mol) of a 40% sodium peroxo disulfate solution is added drop by drop for 4 minutes. The reacting mixture boils already after 2 minutes, whereby the excess heat can be easily discharged by boiling cooling. The following summary shows the time sequence of the exothermic reaction during the addition phase of the oxidation agent.

| Time (min) | 0 | 1 | 1.5 | 2 | 3 | 4 |
|---|---|---|---|---|---|---|
| Temperature (°C.) | 22 | 94 | 99 | 103 | 103 | 104 |

The cooled colorless reaction solution with a pH-value of 0.3 was neutralized with a 33% soda lye and filtered off from the crystallized sodium sulfate and the precipitated iron-III-hydroxide. The quantitative composition of the filtrate was determined by the comparison of the intensities of suitable signals $^1$H-NMR-spectroscopically and showed that 10% 1,1,3-trimethyl-4-sulfomethyl-pyrrolidinium betaine were present in addition to 90% 1,1-dimethyl-3-4-disulfomethyl-pyrrolidinium betaine. (See DD-154 444).

Example 31

This and the following example should illustrate the suitability of combined oxidation agents.

One proceeds in accordance with example 29 and produces a homogenic initial solution with a pH-value 2,1 from dimethyl diallyl ammonium chloride solution, sodium hydrogen sulfite solution and hydrochloric acid and adds at first 10 Mol-% of a 50.0% ammonium peroxo disulfate solution in about 1.5 minutes and subsequently 90 Mol-% 30% hydrogen peroxide are added at such a speed that the exothermic reaction can be controlled by boiling cooling. $^1$H-NMR-spectroscopically showed that the diallyl ammonium salt had been reacted selectively and quantitatively into sulfobetaine sulfonate. The repetition of this test exclusively with hydrogen peroxide as an oxidation agent merely resulted in an oxidation of the sulfite into sulfate in addition to the unchanged initial material and its polymers.

Example 32

One proceeds in accordance with example 31 and chlor is used as the oxidation agent instead of 90 Mol-% hydrogen peroxide, in that the chlor is fed into the reacting mixture that the reaction heat can be very well discharged. $^1$H-NMR-spectroscopically only showed the sulfobetaine sulfonate. The repetition of the test exclusively with chlor as the oxidation agent resulted in sulfate under sulfite oxidation.

Example 33

Sodium-1,1,3,4-tetramethyl-3,4-disulfomethyl-pyrrolidinium-betain from dimethyl-di-2-methallyl ammonium chloride ($R^1=R^2=R^4=R^5=CH_3$; $R^3=-CH_2-SO_3^-$ in the general formula I).

One proceeds as described in example 29 and reacts instead of dimethyl diallyl ammonium chloride 10.64 g (30 mmol) 50% watery dimethyl-di-2-methallyl ammonium chloride solution, 65 mmol 39% and sodium hydrogen sulfite solution and hydrochloric acid as a homogenic solution with an initial pH-value of 2.1 with a 40% sodium peroxo disulfate solution.

The $^{13}$C-NMR-spectrum of the obtained reaction product which was neutralized and substantially separated from sodium sulfate shows that it is not a uniform product-cis/trans-isomeres from 1,1,3,4-tetramethyl-3,4-disulfomethyl-pyrrolidinum-betaine and 1,1,3,3,4-pentamethyl-4-sulfomethyl-pyrrolidinium-betaine.

The chemical displacements are only stated for the cis-compounds. The N—CH$_3$-groups are not equivalent.

x: signals may also be reversed.

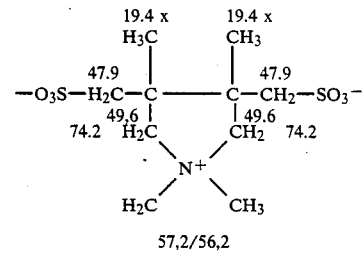

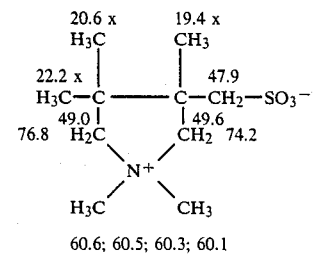

Example 34

Potassium-1-methyl-3,4-disulfomethyl-pyrrolidinium betaine ($R^1=R^4=R^5=H$; $R^2=CH_3$; $R^3=-CH_2-SO_3^-$ in the general formula I) from methyl diallyl ammonium chloride One produces a homogenic solution with a pH-value 2,0 from 1 mol methyl diallyl amine, 1 mol potassium metabisulfite ($K_2S_2O_5$) and 37% hydrochloric acid and proceeds with the aforementioned described example 29.

The sulfobetaine sulfonate was obtained quantitative and showed the following $^{13}$C-NMR-spectrum:

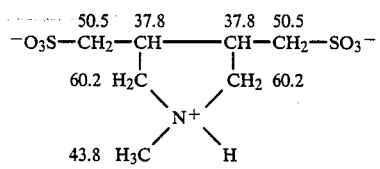

If the free sulfonic acid should be recovered, one can separate them from the inorganic salts and isolate them in accordance with the mode of operation described in example 29.

By neutralisation of the sulfonic acid with one or two mol equivalents of a given base, the given salts of the 1-methyl-3,4-disulfomethyl-pyrrolidinium betaine or the 1-methyl-3,4-disulfomethyl-pyrrolidine may be recovered formula pure.

Example 35

Sodium-3,4-disulfomethyl-pyrrolidinium betaine ($R^1=R^2=R^4=R^5=H$; $R^3=-CH_2-SO_3-$ in the general formula I)

One prepares a homogenic solution with a pH-value of 2.0 from 1 mol diallyl amine, 2 mol sodium hydrogen sulfite and hydrochloride acid and proceeds in accordance with one of the aforedescribed examples. The sulfobetaine sulfonate was obtained in a quantitative yield and showed the following $^{13}$C-NMR-spectrum (cis-configuration):

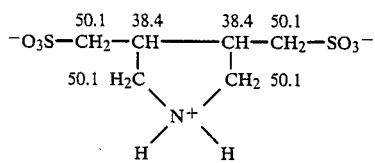

While the chemical displacements for the cis-compounds of the groups $N-CH_2$ and $CH_2-SO_3^-$ collapse at 50.1 ppm, the trans-compound as expected shows 3 signals: 40.4 ppm (CH); 51.0 ppm ($CH_2-SO_3^-$); 53.6 ppm ($N-CH_2$).

If the free sulfonic acid should be recovered, one can separate and isolate the same from the inorganic salts by the mode of process described in example 29. By neutralisation of the sulfobetaine sulfonic acid with one or two molequivalents of a given base, the given salts of the 3,4-disulfomethyl-pyrrolidinium betaine or of the 3,4-disulfomethyl-pyrrolidine may be recovered formula pure.

$^{13}$C-NMR-spectrum of the cis-disodium-3,4-disulfomethyl-pyrrolidine:

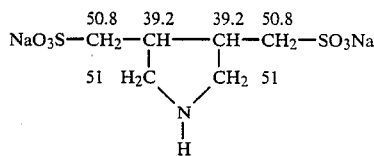

trans-configuration: 42.1 ppm (CH); 52 ppm ($CH_2SO_3Na$); 55 ppm ($N-CH_2$).

Example 36

Sodium-1-benzyl-1-methyl-3,4-disulfomethyl-pyrrolidinium betaine ($R^1-CH_2-C_6H_5$; $R^2=CH_3$; $R^3=-CH_2-SO_3^-$; $R^4=R^5=H$ in the general formula I) from benzyl methyl diallyl ammonium chloride One produces a homogeneous solution with a pH-value of 2,0 from 1 mol 50% benzyl methyl diallyl ammonium chloride solution, 2 mol sodium hydrogen sulfite and hydrochloric acid and one proceeds in accordance with one of the aforedescribed examples.

The sulfobetaine sulfonate was recovered in a quantitative yield and showed the following $^{13}$C-NMR-spectrum:

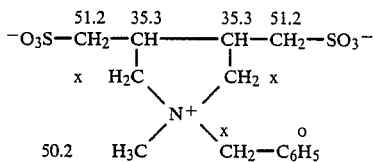

x: 68.3; 68.6; 70.2:
o: 129.5; 130.9 132.3 134

If need be, the free sulfobetaine sulfonic acid can be recovered in accordance with the mode of process described in example 29.

Example 37

Sodium-1-propyl-1-methyl-3,4-disulfomethyl-pyrrolidinium betaine ($R^1=CH_2-CH_2-CH_3$; $R^2=CH_3$; $R^3=-CH_2-SO_3^-$; $R^4=R^5=H$ in the general formula I)

One proceeds in accordance with example 29 and mixes 23.4 g (0.1 mol) propyl methyl diallyl ammonium bromide, 53.4 g (0.2 mol) 39% sodium hydrogen sulfite solution, 4.5 g 37% hydrochloric acid and 47 g water into a homogeneous solution, whose pH-value was 2.0. Finely powdered crystalline potassium peroxo disulfate was added in dosages into this solution within a time span of 7 minutes. The initially redish reaction solution did discolored completely toward the end of the addition of the persulfate.

The exothermic reaction sequence during the dosaging phase of the oxidation agent can be seen from the following summary:

| Time (min)       | 0  | 1  | 2  | 3  | 5  | 6  | 7  |
|------------------|----|----|----|----|----|----|----|
| Temperature (°C.)| 21 | 32 | 48 | 61 | 88 | 92 | 94 |

The $^1$N-NMR-spectrum of the neutralized colorless filtrate showed that the sulfobetaine sulfonate had been recovered in a quantitative yield.

$^{13}$C-NMR spectrum:

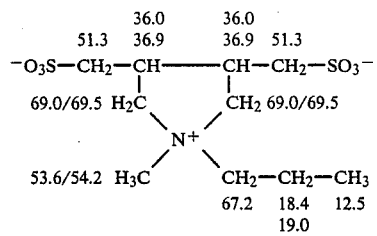

```
        36.0      36.0
  51.3  36.9      36.9  51.3
⁻O₃S—CH₂—CH————CH—CH₂—SO₃⁻
   69.0/69.5 H₂C      CH₂ 69.0/69.5
              \      /
               N⁺
              /    \
  53.6/54.2 H₃C    CH₂—CH₂—CH₃
                   67.2  18.4  12.5
                               19.0
```

The doubling of the signals in the chemical displacements of individual carbon atoms indicates that the sulfobetaine sulfonate is a product mixture from the two possible cis-isomers with respect to the sulfomethyl groups on the 3,4-position.

Examples 38 to 42

Sodium-1-alkyl-1-methyl-3,4-disulfomethyl-pyrrolidinium-betaine ($R^1$=alkyl; $R^2$=CH$_3$; $R^3$=—CH$_2$—SO$_3$; $R^4$=$R^5$=H in the general formula I) from alkyl methyl diallyl ammonium salts.

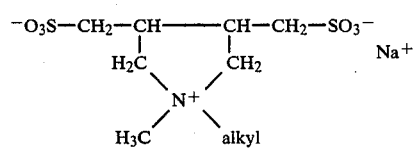

One proceeds in accordance with the aforementioned examples and one produces a homogenous solution with a pH-value of 2.0 to 2.5 from 1 mol alkylmethyl diallyl ammonium salt, 2 mol of a hydrogen sulfite, hydrochloric acid and water.

In the case of the longer chain alkyl methyl diallyl ammonium salts (alkyl>C$_{14}$), the initial suspension had to be heated to about 40° C., so that a homogeneous initial solution was generated and also a too large of a dilution was avoided. After the reaction with 1 mol of a peroxo disulfate or a peroxo disulfate-oxidation agent combination, in particular the longer chain reaction products (alkyl>C$_{12}$) already precipitate during the reaction or from the cooling solution. Depending whether the reaction mixture had been previously neutralized, either the free sulfobetaine sulfonic acid or the corresponding sulfobetaine sulfonates could be separated.

In the case of the short chain sulfobetaine sulfonates, they are either separated from the inorganic accompanying salts either by the method described in example 29 or by extraction of the residue with ethanol/water (ratio 70:30), after evaporating the solution.

TABLE 4

Sodium-1-alkyl-1-methyl-3,4-disulfomethyl-pyrrolidinium betaines

| Examples | $R^1$ (n-alkyl) | point of decomposition (°C.) |
|---|---|---|
| 38 | C$_{10}$H$_{21}$ | 225 |
| 39 | C$_{12}$H$_{25}$ | 215 |
| 40 | C$_{14}$H$_{29}$ | 261+ |
| 41 | C$_{16}$H$_{33}$ | 220 |
| 42 | C$_{18}$H$_{37}$ | 228 |

+free sulfonic acid; its starts to partially decompose at 228° C.;at 261° C. it melts under a complete decomposition.

Example 43

Sodium-1-butyl amino carbonyl methyl-1-methyl-3,4-disulfomethyl-pyrrolidinium betaine ($R^1$=CH$_2$—CO—NH—C$_4$H$_9$; $R^2$=CH$_3$; $R^3$=CH$_2$—SO$_3^-$; $R^4$=$R^5$=H in the general formula I)

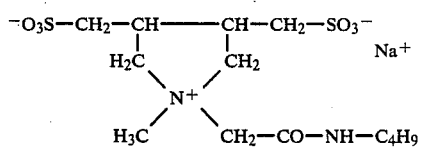

One proceeds in accordance with example 31 and reacts the homogenous solution with a pH-value of 2.0 to 2.5 from 1 mol n-butyl amino carbonyl methyl-methyl diallyl ammonium chloride, which was made from methyl diallyl amine, chlor acetic acid ester and n-butylamine, 2 mol sodium hydrogen sulfite, hydrochloric acid and water with ammonium peroxo disulfate/hydrogen peroxide by using external cooling in such a manner that a reaction temperature of about 50° C. is not exceeded.

After the reaction is completed a neutralisation is immediately performed with soda lye, so as to avoid hydrolysis of the acid amide function. However, if one wishes to react only with peroxo sulfate, analog to example 29, one should, after about 10 Mol-% of the peroxo disulfate solution were added also add simultaneously at least the two molar amount of soda lye together with the remaining amount of peroxo disulfate solution by maintaining a temperature which should not be higher than 50° C.

The sulfobetaine sulfonate (decomposition point>238° C.) was separated by extraction of the residue obtained after the evaporating of the reaction solution with watery ethanol (60%) from the inorganic accompanying salts

Example 44

Sodium-1-dicyclo hexyl amino carbonyl methyl-1-methyl-3,4-disulfomethyl-pyrrolidinium betaine ($R^1$=CH$_2$—CO—N)(C$_6$H$_{11}$)$_2$; $R^2$=CH$_3$; $R^3$=—CH$_2$—SO$_3^-$; $R^4$=$R^5$=H in the general formula I)

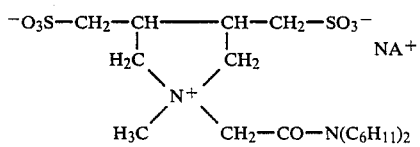

One proceeds in accordance with example 43 and reacts dicyclo hexyl amino carbonyl methyl-methyl diallyl ammonium chloride, which was produced from methyl diallyl amine, chlor acetic acid methyl ester and dicyclo hexyl amine, quantitatively into the sulfobetaine sulfonate (decomposition point>270° C.).

Example 45

Sodium-1-dodecyl/tetradecyl amino carbonyl methyl-1-methyl-3,4-disulfomethyl-pyrrolidinium betaine ($R^1=CH_2-CO-NH-C_{12}H_{25}/C_{14}H_{29}$; $R^2=CH_3$; $R^3=CH_2-SO_3^-$; $R^4=R^5=H$ in the general formula I)

$$\begin{array}{c} ^-O_3S-CH_2-CH\underline{\quad\quad}CH-CH_2-SO_3^- \\ \quad\quad\quad\quad | \quad\quad\quad\quad\quad\quad | \\ \quad\quad\quad\quad H_2C\quad\quad\quad\quad\quad CH_2 \quad\quad Na^+ \\ \quad\quad\quad\quad\quad\searrow N^+ \swarrow \\ \quad\quad\quad H_3C\quad\quad\quad CH_2-CO-NH-C_{12}H_{25}/C_{14}H_{29} \end{array}$$

One proceeds in accordance with example 43 and reacts dodecyl/tetradecyl-amino carbonyl methyl-methyl diallyl ammonium chloride, which was produced from methyl diallyl amine, chlor acetic acid methyl ester and dodecyl/tetradecyl amine-mixture (cocos amine, component ratio about 1:1), quantitatively into sulfobetaine sulfonate (decomposition point>246° C.).

Example 46

Sodium-1/di-(dodecyl/tetradecyl amino carbonyl)/methyl-1-methyl-3,4-disulfomethyl-pyrrolidinium betaine ($R^1=CH(CO-NH-C_{12}H_{25}/C_{14}H_{29})$; $R^2=CH_3$; $R^3==-CH_2-SO_3$; $R^4=R^5=H$ in the general formula I)

$$\begin{array}{c} ^-O_3S-CH_2-CH\underline{\quad\quad}CH-CH_2-SO_3^- \\ \quad\quad\quad\quad | \quad\quad\quad\quad\quad\quad | \\ \quad\quad\quad\quad H_2C\quad\quad\quad\quad CH_2 \quad\quad Na^+ \\ \quad\quad\quad\quad\quad\searrow N^+ \swarrow \\ \quad\quad\quad H_3C\quad\quad\quad CH(CO-NH-C_{12}H_{25}/C_{14}H_{29})_2 \end{array}$$

One proceeds in accordance with example 42 and reacts di-(dodecyl/tetradecyl amino carbonyl)methyl-methyl diallyl ammonium bromide, which had been produced from methyl diallyl amine, brome malonic acid diethyl ester and dodecyl/tetradecyl amine-mixture (coconut amines, component ratio 1:1), at a reaction temperature of 40° C. into sulfobetaine sulfonate (melting point 139° to 148° C., recrystilation from ethanol).

Example 47

Sulfocyclosulfination of triallyl amine hydrochloride into trisodium-1-(2'-sulfinato-3'-sulfo)propyl-3-sulfinato-methyl-4-sulfomethyl-pyrrolidinium betaine $(R^1 = CH_2-\underset{|}{C}H-CH_2-SO_3^-, R^2 = R^4 = R^5 = H;$
$\quad\quad\quad\quad SO_2^-$ $R^3 = -CH_2-SO_2-$ in the general formula I)

13.7 g (0.1 mol) fresh distilled triallyl amine is added, under cooling, to a mixture of 12 g 37% hydrochloric acid and 10 g water in a sulfonation flask provided with a stirrer, a thermometer and a glass electrode. Thereafter, the hydrochloric acid triallyl amine hydrochloride solution with 108.7 g (0.425 mol) 40.7% technical sodium hydrogen sulfite solution with an iron content of 60 mg/l. The homogenous pale yellow initial solution has a pH-value of 2.1. 1.08 g (4 Mol-%) finely powdered potassium peroxo disulfate are added under stirring, whereby the peroxo disulfate dissolves instantly, the reacting mixture heats up and assumes a blood red color. The time sequence of the exothermic sulfocyclosulfination is shown in the following summary:

| Time (s)    | 0  | 20 | 30 | 40 | 60 |
|-------------|----|----|----|----|----|
| Temp. (°C.) | 23 | 35 | 63 | 68 | 67 |

The reaction is completed after reaching the temperature maximum. The red coloring of the reaction mixture is caused by the use of iron containing technical chemicals which form iron-III-sulfinate. The solution can be decolored by adding suitable complex formers. One proceeds as follows for isolating the free acid 1-(2'-sulfinic acid-3'-sulfonic acid)propyl-3-sulfinic acid methyl-4-sulfomethyl-pyrrolidinium betaine:

The reaction solution is reduced in a vacuum by driving off SO2, is brought to the pH-value 7 with a small amount of soda lye, some drops of hydrogen peroxide solution is added and the precipitated iron-III-hydroxide is filtered off.

The product is received in concentrated hydrochloric acid and the sodium chloride is separated by filtration, after reducing the filtrate to a dry state. The reducing of the hydrochloric acid solution and the subsequent addition of ethanol delivers the free sulfinic acid.

$^{13}$C-NMR-spectrum (D2O, external standard TMS):

$$\begin{array}{c} \quad\quad 57/59\ \ 36/38\quad\quad 36/38\ \ 50/51 \\ HO_2S-CH_2-HC\underline{\quad\quad}CH-CH_2-SO_3^- \\ \quad\quad\quad\quad | \quad\quad\quad\quad\quad\quad | \\ \quad 57/59\ H_2C\quad\quad\quad CH_2\ 57/59 \\ \quad\quad\quad\quad\searrow N^+ \swarrow\quad 54/55\ \ 57/59\ \ 48.6 \\ \quad\quad\quad H\quad\quad\quad CH_2-CH-CH_2-SO_3H \\ \quad\quad\quad\quad\quad\quad\quad\quad\quad\quad\quad | \\ \quad\quad\quad\quad\quad\quad\quad\quad\quad\quad\quad SO_2H \end{array}$$

The statements for the numbers on the atom symbols correspond to the chemical displacements in ppm.

A correct signal association was not made, since the sulfobetaine sulfon-disulfinic acid is present as a cis-/trans-isomer mixture (four isomeres).

Example 48

Sulfocyclosulfination of N,N,N-triallyl-ammonio-acetic acid-dodecyl/tetradecyl amide-chloride into trisodium-1-dodecyl/tetradecyl amino carbonyl methyl-1-(2'-sulfinato-3'-sulfo)propyl-3-sufinatomethyl-4-sulfomethyl-pyrrolidinium betaine $(R^1 = -CH_2-\underset{|}{C}H-CH_2-SO_3^-;$
$\quad\quad\quad\quad\quad\quad\quad SO_2^-$ $R^2=CH_2-CO-NH-C_{12}H_{25}/C_{14}H_{29}$;
$R^3=-CH_2-SO_2^-$; $R^4=R^5=H$ in the general formula I)

At first the synthesis of the initial product N,N,N-triallyl-ammonio-acetic acid methyl ester-chloride will be described:

13.7 g (0.1 mol) fresh distilled triallyl amine and 10.85 g (0.1 mol) acid free chlor acetic acid methyl ester are heated in 30 ml methanol until the pH-value of the reaction solution has dropped to 7.

N,N,N-triallyl-ammonio-acetic acid-dodecyl/tetradecyl amide-chloride

A solution of 19.9 g (0,1 mol) dodecyl/tetradecyl amine-mixture (coconut amines, component ratio 1:1) and 100 ml methanol are added to the aforementioned methylester chloride, whereupon the solution is again heated until reaching a pH-value of about 7. Subsequently, the methanol is distilled off under a reduced pressure and the remaining residue is used for the sulfocyclosulfination.

One proceeds as described in example 47, in that 0.1 mol of the aforementioned prepared dodecyl/tetradecyl amide chloride is received in 0.42 mol of a 40,7% technical sodium hydrogen sulfite solution and 80 g water and adjust the pH-value to 2.0 with concentrated hydrochloric acid. 4 Mol-% of a 50% ammonium peroxo disulfate solution is added to the obtained milky-white initial solution of 32° C. A part of the reacted product starts to precipitate from the reacting solution already after 15 seconds.

The total time sequence of the exothermic sulfocyclosulfination is shown in the following summary:

| Time | 0 | 15 | 35 | 60 | 80 | 120 |
|---|---|---|---|---|---|---|
| Temperature (°C.) | 32 | 35 | 42 | 49 | 50 | 49 |

The reaction mixture is neutralized with soda lye, after the reaction had been completed, and while cooling the sulfobetaine disulfinate-sulfanate it crystallizes into beige colored mass which can be easily separated from the mother liquor, and the reaction is almost quantitative.

One receives a product which is completely colorless, crystalline, as well as free from inorganic salts and iron-III-hydroxide with a melting point decomposition >216° C., if the neutralized raw product from ethanol is recrystallized.

The free sulfobetaine-disulfinic acid sulfonic acid can be easily isolated in a crystalline manner, if one adds the equivalent amount of concentrated hydrochloric acid to the hot saturated solution of the trisodium salt and by cooling it.

Example 49

Sulfocyclosulfination of
N,N,N,-triallyl-ammonio-acetic acid-octadecyl amide-chloride into trisodium-1-octadecyl-amino carbonyl
methyl-1-(2'-sulfinato-3'-sulfo)propyl-3-sulfinato methyl-4-sulfomethyl-pyrrolidinium betaine

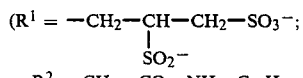
$R^2 = CH_2-CO-NH-C_{18}H_{37}$;

$R^3 = -CH_2-SO_2^-$; $R^4 = R^5 = H$ in the general formula I)

One proceeds in accordance with example 47 and receives 0,1 mol N,N,N-triallyl-ammonio-acetic acid-octadecyl amide-chloride (produced from triallyl amine, chlor acetic acid methyl ester and octadecyl amine in accordance with the specification stated in example 48) in 108.7 g (0.425 mol) 40.7% technical sodium hydrogen sulfite solution and 140 g water under heating. One adjusts the pH-value to 2.0 with 37% hydrochloric acid and adds 4 Mol-% of a 30% sodium peroxo disulfite solution to the initial solution of 49° C. The time and temperature sequence of the sulfocyclosulfination reaction is shown in the following summary:

| Time (s) | 0 | 15 | 30 | 80 | 150 | 180 |
|---|---|---|---|---|---|---|
| Temperature (°C.) | 49 | 59 | 62.5 | 63 | 63 | 62.5 |

The end product starts to separate from the reaction solution as a beige colored mass during the reaction and can be quantitatively separated from the mother liquor after cooling. The further purification of the sulfinate or the isolation of the free sulfobetaine-disulfinic acid-sulfonic acid may be performed analog to the processes described in example 48. Melting point of the sulfobetaine-disulinic acid-sulfonic acid (ethanol) 98° C.

Examples 50 to 52

Sulfocyclosulfination of alkyl triallyl ammonium bromide into trisodium-7-alkyl-1-(2'-sulfinato-3'-sulfo)propyl-3-pyrrolidinium betaine

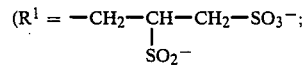

$R^2$=alkyl; $R^3$=—$CH_2$—$SO_2^-$; $R^4=R^5=H$ in the general formula I)

One proceeds in accordance with one of the aforedescribed examples and reacts the combined solutions with a pH-value of 2.0 from the given alkyl triallyl ammonium bromide and sodium hydrogen sulfite with ammonium- or alkali peroxo disulfate. In particular the octadecyl-sulfobetaine-disulfinic acid-sulfonic acid starts to crystallize from the cooling reaction solution, after the sulfocyclosulfination and can be easily separated from the mother liquor and, if need be, can be easily purified in accordance with the aforedescribed processes. The shorter chain sulfocyclosulfination products are neutralized with 33% soda lye and, if need be, may be separated from the inorganic salts by extraction of their evaporated solution with ethanol/water (2:1).

| Example | $R^2$ (alkyl) | Melting point (°C.) |
|---|---|---|
| 50 | $C_8H_{17}$ | decomposition > 244 |
| 51 | $C_{12}H_{25}$ | decomposition > 226 |
| 52 | $C_{18}H_{37}$ | 118+ |

+as sulfobetaine-disulfinic acid-sulfonic acid

Example 53

Sulfocyclosulfination of tetra allyl ammonium bromide

One proceeds as described in example 47 and reacts a homogeneous solution (pH-value 2.3) of 25.8 g (0.1 mol) crystalline tetraallyl ammonium bromide, 25.8 g water and 112 g (0.42 mol) of a 39% technical sodium hydrogen sulfite solution as well as 4.5 g 37% hydrochloric acid with 1.08 g (4 Mol-%) finely powdered potassium peroxo disulfate.

The time sequence of the exothermic sulfocyclosulfination is shown in the following summary:

| Time (s) | 0 | 15 | 30 | 40 | 60 | 120 |
|---|---|---|---|---|---|---|
| Temperature (°C.) | 28 | 29 | 41 | 71 | 72 | 71 |

The pH-value was reduced to 2.0, after the reaction had been completed. For removing excess sulfur dioxide one distills 1 to 2 ml water under reduced pressure and adjusts the pH-value of the solution to 7 with 33% soda lye.

The following $^{13}$C-NMR-spectrum from trisodium salt of the isomeric spiro-sulfobetaine-disulfinic sulfonic acids (D$_2$O, external standard TMS):

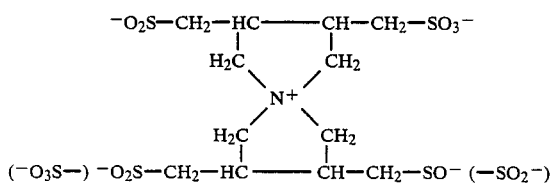

The statements of the numbers correspond to the chemical displacements in ppm (in parenthesis the statements for the trans-linked isomeres).

| —CH | : 35.0; 35.2; 36.7 (38.6; 40.7) |
|---|---|
| —CH$_2$SO$_3^-$ | : 51.8; 51.8 |
| —CH$_2$SO$_2^-$ | : 61.3; 61.5 |
| —CH$_2$N+ | : 69.6; 69.9; 70.8 |

The chemical displacements for the individual building groups appears repeatedly, since for the cis-(sulfomethyl- or sulfinato methyl groups) compounds two diasteriomeres are possible.

Example 54

Trisodium-1-methyl-1-(2',3'-disulfo)propyl-3,4-disulfomethyl-pyrrolidinium betaine

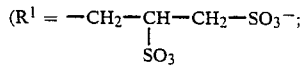

R$^2$=CH$_3$; R$^3$=—CH$_2$—SO$_3^-$; R$^4$=R$^5$=H in the general formula I) from methyl triallyl ammonium chloride 238 g (0.5 mol) 39.43% watery methyl triallyl ammonium chloride solution, 533.6 g (2 mol) 39% technical watery sodium hydrogen sulfite solution with an iron content of 9 mg/mol solution as well as 35 g 37% hydrochloric acid are admixed into a homogeneous solution, whose pH-value was 2.0 (glass electrode). 40% of a watery sodium peroxo disulfate solution, which was prepared from 238.1 g (1 mol) and 357.15 g water is efficiently added to the prepared pale yellow initial solution. About 50% of this solution was added after 1.5 minutes.; the mixture, which in the meantime assumed a blood red color, had heated up from 21° to 100° C. and started to boil. The addition of the oxidation agent was continued, whereby the reaction solution became increasinly lighter in color and finally became yellow, after about 70% of the peroxo disulfate solution had been added. The adding of the peroxo disulfate solution was completed after 4 minutes, whereby the reaction heat could be easily discharged by boiling cooling.

The following summary shows the time sequence of the exothermic reaction during the adding phase of the oxidation agent:

| Time (min) | 0 | 0.5 | 1 | 1.5 | 3 | 4 |
|---|---|---|---|---|---|---|
| Temperature (°C.) | 21 | 65 | 80 | 100 | 102 | 98 |

A $^1$H-NMR spectrum prepared from the solution at this point in time acknowledged the quantitative and selective reaction of the methyl triallyl ammonium chloride into the sulfobetaine trisulfonate. After neutralisation of the heavy acid reaction solution with 33% soda lye the iron salt, which was contained therein because of the use of technical sodium hydrogen sulfite solution, flocculated as iron-III-hydroxide and could be filtered out together with the larges portion if the crystallized sodium sulfate. The colorless filtrate showed the following $^{13}$C-NMR-spectrum:

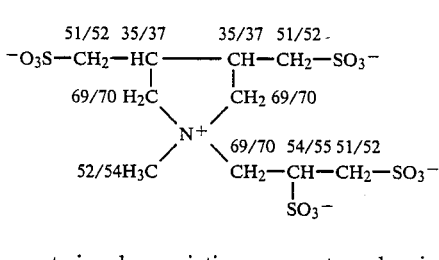

An exact signal association was not made, since the sulfobetaine-trisulfonic acids is present as cis/trans-isomeric mixture (three isomers).

However, if the pH-value of the homogeneous initial solution is adjusted to values of >2.5, the selectivity of the reaction in process decreases, whereby to an increasing degree in addition to 1-methyl-1-(2',3'-disulfo)-propyl-3,4-disulfomethyl-pyrrolidinium betaine also 1,3-dimethyl-1-(3'-sulfopropyl)-4-sulfomethyl-pyrrolidinium betaine (see DD-WP 200 739, example 2) is formed which finally may become the main product of the reaction.

Example 55

1-(2',3'-disulfonic acid)propyl-3-sulfonic acid methyl-4-sulfomethyl-pyrrolidinium betaine

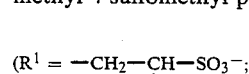

R$^2$=R$^4$=R$^5$=H; R$^3$=—CH$_2$—SO$_3^-$ in the general formula I) from triallyl amine hydrochloride One proceeds as described in example 54 and admixes 13.72 g (0.1 mol) triallyl amine, 16 g water, 16 g 37% hydrochloric acid as well as 106.8 (0.4 mol) 39% sodium hydrogen sulfite solution into a homogeneous solution, whose pH-value was 2.0. Into this solution 0.2 mol of a 40% sodium peroxo disulfate solution is added drop by drop within 2.5 minutes. The following summary indicates the time sequence of the exothermic reaction during the adding phase of the oxidation agent:

| Time (min) | 0 | 0.5 | 1 | 1.5 | 2.5 |
|---|---|---|---|---|---|
| Temperature (°C.) | 22 | 70 | 90 | 104 | 104 |

The initially pale yellow solution become blood red soon after the addition of the peroxo disulfate, but it became gradually light and at the end it became clear yellow. At this point in time the reaction was performed quantitatively and selectively into sulfobetaine trisulfonate, as could be shown $^1$H-NMR-spectroscopically.

However, if the sulfobetaine trisulfonic acid should be completely separated from their accompanying salts, one can proceed as follows:

After reducing the aforementioned recovered reaction into a dry state, the received salt residue is reacted with the sufficient amount of concentrated hydrochloric acid and is well processed, it is filtered off from the undissolved sodium salts and the hydrochloric acid solution of the sulfobetaine trisulfonic acid is evaporated under reduced pressure. The sulfonic acid can be precipitated by adding ethanol to the remaining residue.

$^{13}C$-NMR -spectrum

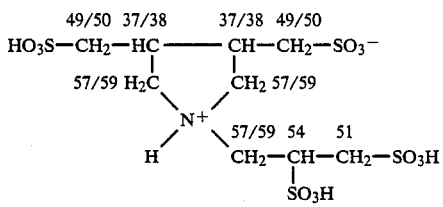

An exact signal association was not made, since the sulfobetaine trisulfonic acid is present as a cis/trans-isomeric mixture (three isomers).

Example 56

This example should illustrate the suitability of oxidation agent combinations:

One proceeds in accordance with example 56 and produces a homogeneous initial solution with a pH-value of 2.0 from 0.1 mol triallyl amine, 0.4 mol sodium hydrogen sulfite, hydrochloric acid and water. At first, 15 Mol-% of a 50% ammonium peroxo disulfate solution and finally 85 Mol-% 30% hydrogen peroxide are added in about 1.5 minutes with such a speed that the exothermic reaction could be controlled by boiling cooling, for which 3.5 minutes were required. $^1$H-NMR-spectroscopically it could be shown that the triallyl amine hydrochloride has been reacted quantitatevely into sulfobetaine trisulfonate.

The repetition of the test exclusively with hydrogen peroxide as an oxidation agent resulted in addition to the unchanged initial material and polymer constituents merely to an oxidation of the sulfite into sulfate.

Example 57

Trisodium-1-octyl-1-(2',3'-disulfo)propyl-3,4-disulfomethyl-pyrrolidinium betaine

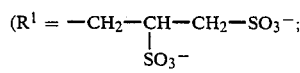

$R^2 = C_8H_{17}$; $R^3 = -CH_2-SO_3^-$; $R^4 = R^5 = H$ in the general formula I) from octyl triallyl ammonium bromide.

One proceeds in accordance with one of the aforedescribed examples and converts a homogeneous solution with a pH-value of 2.0 from 1 mol octyl triallyl ammonium bromide, 4 mol of a hydrogen sulfite, hydrochloric acid and water with 2 mol of a 50% ammonium peroxo disulfate solution.

Since the free sulfobetaine trisulfonic acid did not separate from the reaction solution, the solution was neutralized with a 33% soda lye, filtered, evaporated into a dry state and the sulfobetaine trisulfonate with the decomposition point >264° C. is separated with an ethanol/water mixture (1:1) from the inorganic salts.

Example 58

1-tetradecyl-1-(2',3'-disulfo)propyl-3-sulfonic acid methyl-4-sulfomethyl-pyrrolidinium betaine

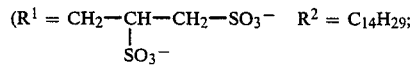

$R^3 = -CH_2-SO_3^-$; $R^4 = R^5 = H$ in the general formula 1) from tetradecyl triallyl ammonium bromide One proceeds in accordance with one of the aforedescribed examples and reacts 1 mol tetra decyl triallyl ammonium bromide with sodium peroxo disulfate. During the reaction the sulfobetaine trisulfonic acid started to flocculate from the heavy acid reaction solution in yellowish brown flakes.

After recrystallisation (ethanol) the sulfobetaine trisulfonic acid with a melting point of 162° C. (decomposition) was obtained.

Example 59

Trisodium-1-dodecyl/tetradecyl amino carbonyl methyl-1-(2',3'-disulfo)propyl-3,4-disulfomethyl-pyrrolidinium betaine

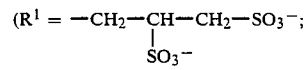

$R^2 = CH_2-CO-NH-C_{12}H_{25}/C_{14}H_{29}$; $R^3 = -CH_2-SO_3^-$; $R^4 = R^5 = H$ in the general formula I)

One proceeds in accordance with one of the aforedescribed examples and reacts the homogenous solution with a pH value of 2.0 from 1 mol dodecyl/tetradecyl amino carbonyl methyl-triallyl-ammonium chloride, which was made from triallyl amine, chlor acetic acid methyl ester and dodecyl/tetradecylamine-mixture (cocos amine, component ratio about 1:1), as well as 4 mol sodium hydrogen sulfite and hydrochloric acid with sodium peroxo disulfate/hydrogen peroxoxide by using external cooling in such a manner that the reaction temperature did not exceed 60° C. After the reaction is completed a neutralisation is immediately performed with 33% soda lye, so as to avoid a hydrolysis of the acid amide function.

However, if one wishes to react only with peroxo disulfate in accordance with example 54, one should, after about 10 Mol-% of the peroxo disulfate solution had been added to the triallyl ammonium salt, add at least double of the molar amount of soda lye simultaneously with the remaining peroxo disulfate by maintaining a temperature of abot 60° C.

The sulfobetaine trisulfonate which was obtained in a quantitative yield was separated and recrystallized from the inorganic salts with an ethanol/water mixture (2:1), after reducing the reaction solution to a dry state. The point of decomposition of the trisodium salt is at >252° C.

Example 60

Trisodium-1-octadecyl amino carbonyl methyl-1-(2',3'-disulfo)propyl-3,4-disulfomethyl-pyrrolidinium betaine

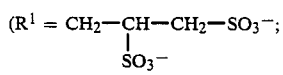

$R^2 = -CH_2-CO-NH-C_{18}H_{37}$; $R^3 = -CH_2-SO_3^-$; $R^4 = R^5 = H$ in the general formula I).

One proceeds in accordance with example 59 and quantitativly reacts octa decyl amino carbonyl methyl-triallyl ammonium chloride, which was made from triallyl amine, chlor acetic acid methyl ester and octadecyl amine, into sulfobetaine trisulfonate. The trisodium salt was separated from the inorganic salts by an ethanol/water mixture (2:1), after the reaction mixture had been reduced to a dry state. It decomposes at >248° C.

Example 61

Trisodium-1,1-(2',3'-disulfomethyl)tetramethylene-3,4-disulfomethyl-pyrrolidinium betaine from tetraallyl ammonium bromide One proceeds as described in example 54 and reacts a homogeneous solution with an initial pH-value 2.05 from 25.8 g (0,1 mol) of crystalline tetraallyl ammonium bromide, 25.8 g water, 8.3 g 37% hydrochloric acid and 106.8 (0.4 mol) 39% sodium hydrogen sulfite solution with 119.05 g (0.2 mol) 40% sodium peroxo disulfate solution in 4.5 minutes. The time sequence of the exothermic reaction during the adding phase of the peroxo disulfate is shown in the following summary:

| Time (min) | 0 | 1 | 2 | 3 | 4 | 4.5 |
|---|---|---|---|---|---|---|
| Temp. (°C.) | 26 | 82 | 96 | 101 | 101 | 100 |

At this point in time the tetraallyl ammonium bromide was already quantitatively reacted to the end product, as could be noted by the $^1$H-NMR-spectrum.

After the reaction solution had been neutralized with soda lye and had been stored in the refrigerator and also was subsequently separated from the flocculated iron-III-hydroxide and crystallized sodium sulfate hydrates, a colorless crystalline powder was obtained from the filtrate, after distilling of the water, with the following $^{13}$C-NMR-spectrum:

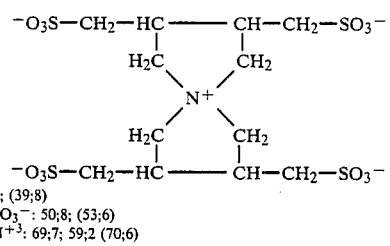

—CH: 36;4; (39;8)
—CH$_2$—SO$_3^-$: 50;8; (53;6)
—CH$_2$—N$^{+3}$: 69;7; 59;2 (70;6)

The statements of the numbers correspond to the chemical displacements for the trans-linked isomers.

Example 62

Disodium-1-methyl-1-(3'-sulfo)propyl-3-sulfinatomethyl-4-sulfomethyl-pyrrolidinium betaine
($R^1=-CH_2-CH_2-CH_2-SO_3^-$; $R^2=CH_3$; $R^3=-CH_2-SO_2^-$; $R^4=R^5=H$ in the general formel I) by sulfocyclosulfination of methyl triallyl ammonium chloride.

95.2 g (0,2 mol) 39.43% watery methyl triallyl ammonium chloride solution and 162.8 g (0.61 mol) 39% technical watery sodium hydrogen sulfite solution with an iron content of 9 mg/mol solution are admixed to a homogeneous solution with a pH-value of 4.3. 1.9 g (4 Mol-%)sodium peroxo disulfate is added to the pale yellow initial solution by stirring, whereby the peroxo disulfate immediately dissolves, while the reacting mixture heats up and assumes an orange color.

The time sequence of the exothermic sulfocyclosulfination is shown by the following summary:

| Time (s) | 0 | 15 | 25 | 40 | 60 |
|---|---|---|---|---|---|
| Temperature (°C.) | 23 | 42 | 61 | 64 | 63 |

The reaction is completed after the maximum temperature is reached. The $^1$H-NMR-spectrum of the reaction solution showed the quantitative sulfocyclosulfination of the methyl triallyl ammonium chloride. The sulfobetaine-sulfinate-sulfonate was received in a 50% to 60% yield in addition to the sulfobetaine-disulfinate-sulfonate and the sulfobetaine-sulfonate.

For separating the free sulfinic acid-sulfonic acid, one proceeds as follows:

After reducing the aforementioned recovered reaction solution in a dry state under a reduced pressure, the recovered salt residue had been reacted with a sufficient amount of concentrated hydrochloric acid and well processed, filtered off from the insoluble sodium chloride and again reduced under reduced pressure. The sulfocyclosulfination product can be precipitated by adding alcohol to the remaining oily residue.

The $^{13}$C-NMR-spectrum of the hydrochloric acid residue showed that the chemical displacements (ppm) of individual signals of the carbon atom have doubles which proves the presence of the following structural isomers.

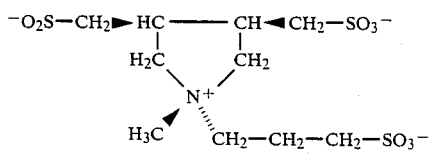

-continued

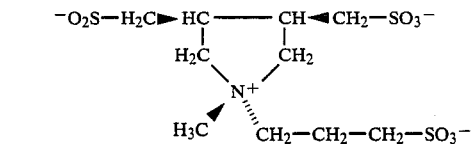

N—CH₂ (ring): 69;2; 69;5
N—CH₂: 63;6; 66;5
CH₂—SO₂⁻: 57;1; 57;3
N—CH₃: 50;8; 53;1
CH₂—SO₃⁻ (ring): 51;1; 51;3
CH₂—SO₃⁻: 49;2
C̲H̲—CH₂—SO₃⁻: 36;0; 36;8
C̲H̲—CH₂—SO₂⁻: 33;0; 33;9
CH₂: 20;5; 21;1

A product obtained in accordance with the aforementioned mode of process by sulfocyclosulfination of methyl diallyl-3-sulfopropyl-ammonium betaine (see DD-PS 200 739) with a pH-value of 2.5 with the two molar amount of hydrogen sulfite and 4 Mol-% peroxo disulfate showed an identical $^{13}$C-NMR-spectrum

Example 63

One proceeds in accordance with example 62 and admixes 0.2 mol methyl triallyl ammonium chloride, 0.6 mol sodium hydrogen sulfite solution and 14 g 33% soda lye into a homogeneous mixture with a pH-value of 5.4 and add 4 Mol-% potassium peroxo disulfate. The sulfobetaine-sulfinate-sulfonate was obtained as a reaction product by about ⅔ and the sulfobetaine-sulfonate by about ⅓.

Example 64

One proceeds in accordance with example 62 and admixes 0.2 mol methyl triallyl ammonium chloride solution, 0.7 mol sodium hydrogen sulfite solution and 2.8 g 37% hydrochloric acid into a homogeneous solution and 4 Mol-% of ammonium peroxo disulfate are added. The sulfobetaine-sulfinate-sulfonate as well as the sulfobetaine-disulfinate-sulfonate were obtained as the reaction product in about equal parts in addition to a low amount of about 5% of the sulfobetaine sulfonate.

Example 65

This example should demonstrate the possibility that perodoxo disulfate can be used for initiating the sulfocyclosulfination also with other oxidation agent, like air, if less than about 1 Mol-% peroxo disulfate is used. In contrast to example 62 the reaction time until the complete reaction is considerably prolonged.

In a sulfonation flask in accordance with example 62, which was additionally provided with a gas input tube, the initial solution described in this example with a pH-value of 4.3 from 0.2 Mol methyl triallyl ammonium chloride solution and 0.61 mol sodium hydrogen sulfite solution was made and prepared. Under vigorous stirring, a weak air current is fed through the solution in such a manner that air bubbles are constantly finely dispersed therein and simultaneously 333 mg (0.7) Mol-%) sodium peroxo disulfate is added, which previously had been dissolved in 2 g of water. Immediately after the peroxo disulfate is added the pale yellow solution assumes a light orange color, but after 3 minutes it again had assumed its original coloring. The reacting mixture heats from 25° to 50.5° C., which is the maximum temperature, within 16 minutes after the start of the reaction, but cools gradually during the continues stirring.

The total time sequence of the exothermic sulfocyclosulfination with the oxidation agent mixture is shown in the following summary:

| Time (min) | 0 | 1 | 1.5 | 2 | 5 | 11 | 16 | 20 | 80 | 140 |
|---|---|---|---|---|---|---|---|---|---|---|
| Temperature (°C.) | 25 | 40 | 43 | 45 | 48 | 50 | 50.5 | 50 | 37 | 30 |

At the point in time when the maximum temperature was reached, the reaction was not yet completed, only 4 hours later no triallylammonium salt could be no longer shown $^1$H-NMR-spectroscopically. At the end of the reaction the pH-value of the reaction solution was increased to 5.2. The composition of the product mixture did correspond to the one of example 62.

Example 66

Disodium-1-tetradecyl-1-(3'-sulfo)propyl-3-sulfinato-methyl-4-sulfomethyl-pyrrolidinium betaine ($R^1$=—CH₂—CH₂—CH₂—SO₃⁻, $R^2$=C₁₄H₂₉; $R^3$=—CH₂—SO₂⁻; $R^4$=$R^5$=H in the general formula I) by sulfocyclosulfination of tetradecyl triallyl ammonium bromide One proceeds in accordance with example 62 and reacts the homogeneous solution with a pH-value of 4.5 from 0.1 mol tetradecyl triallyl ammonium bromide and 0.3 mol sodium hydrogen sulfite with 4 Mol-% potassium peroxo disulfate. The neutralized clear reaction solution may be used as is for further reactions or, if need be, may be reduced to a dry state, so as to separate the sulfonation product from the inorganic salts by means of ethanol/water (2:1). The extraction product which had been recrystallized with ethanol/water did decompose at a temperature above 270° C.

Example 67

Disodium-1-dodecyl/tetradecyl-amino carbonyl methyl-1-(3'-sulfo)propyl-3-sulfinatomethyl-4-sulfomethyl-pyrrolidinium betaine ($R^1$=—CH₂—CH₂—CH₂—SO₃⁻; $R^2$=CH₂—CO—N-H—C₁₂H₂₅/C₁₄H₂₉; $R^3$=—CH₂—SO₂⁻; $R^4$=$R^5$=H in the general formula I) by sulfocyclosulfination of dodecyl/tetradecyl amino carbonyl methyl-trially ammonium chloride One proceeds in accordance with example 65 and reacts dodecyl/tetradecyl-amino carbonylmethyl-triallyl ammonium chloride, which had been produced from triallyl amine, chlor acetic acid methyl ester and dodecyl/tetradecyl amine-mixture (Cocos amine, component ratio 1:1) into sulfobetaine-sulfinate-sulfonate mixture.

The extraction product which had been recovered from the evaporated reaction solution with ethanol/water (2:1), which again is recrystallized with ethanol/water did melt at 212° C. under decomposition.

Example 68

Disodium-1-methyl-1-(3′-sulfo)propyl-3,4-disulfomethyl-pyrrolidinium betaine
($R^1$=—$CH_2$—$CH_2$—$CH_2$—$SO_3^-$; $R^2$=$CH_3$;
$R^3$=—$CH_2$—$SO_3^-$; $R^4$=$R^5$=H in the general formula 1) from methyl triallyl ammonium chloride 95.2 g (0.2 mol) 39.43% watery methyl triallyl ammonium chloride solution, 160.1 (0.6 mol) 39% watery technical sodium hydrogen sulfite solution with an iron content of 9 mg/mol solution as well as 3 drops of a 33% soda lye were admixed into a homogeneous solution, whose pH-value was 4.5 (glass electrode). A 40% watery sodium peroxo disulfate solution, which had been prepared from 47.62 g (0.2 mol) and 71.4 g water, had been added efficiently to the prepared pale yellow initial solution. After 2.5 minutes about 50% of the peroxo disulfate solution had been added; the mixture which in the meantime had assumed a light orange mixture did heat from 23° to 101° C. and boiled. The addition of the oxidation agent had been continued in such a manner that the reaction heat could be easily discharge by boiling cooling.

During the further addition of the peroxo disulfate solution the reaction mixture increasingly became lighter and the end, after 3.5 minutes, it was practically colorless.

The following summary shows the time sequence of the exothermic reaction during the adding phase of the oxidation agent:

| Time (min)        | 0  | 1  | 2  | 2.5 | 3   | 3.5 |
|-------------------|----|----|----|-----|-----|-----|
| Temperature (°C.) | 23 | 80 | 93 | 101 | 101 | 100 |

The $^1$H-NMR-spectrum of the reaction solution showed the quantitive sulfonation of the methyl triallyl ammonium chloride.

The sulfobetaine disulfonate had been received as a yield in addition to the sulfobetaine trisulfonate and the sulfobetaine sulfonate in an amount of 50 to 60%. After neutralisation of the heavy acid reaction solution with a 33% soda lye the iron salt contained therein, because of the use of technical sodium hydrogen sulfite solution, flocculated as an iron-III-hydroxide and could be filtered off with a large part of the crystallyzed sodium sulfate. The $^{13}$C-NMR-spectrum of the colorless filtrate did show that the chemical displacements (ppm) of individual carbon atoms did have duplications, which proves the presence of the following structure isomeres:

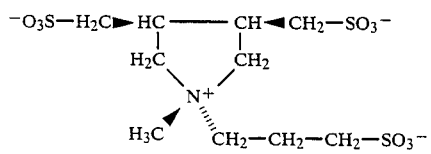

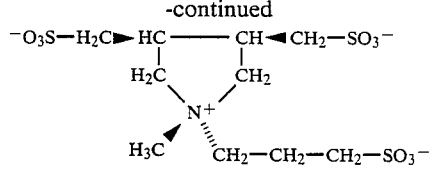

N—$CH_2$ (ring): 69;0; 69;5
N—$CH_2$: 66;5; 63;6
N—$CH_3$: 53;2
$CH_2$—$SO_3^-$ (ring): 51;0
$CH_2$—$SO_3^-$: 49;2
CH: 36;6; 35;8
$CH_2$: 21;2; 20;7

A product obtained in accordance with the aforementioned mode of process by sulfonation of methyl-diallyl-3-sulfopropyl-ammonium betaine (see DDP-WP 200 739) with a pH-value of 2.5 with the two molar amount of hydrogen sulfite and the molar amount of peroxo disulfate did show an identical $^{13}$C-NMR-spectrum

Example 69

One proceeds in accordance with example 68 and admixes 0.2 mol methyl-triallyl ammonium chloride solution, 0.6 mol sodium hydrogen sulfite solution and 14 g 33% soda lye into a homogeneous solution with a pH-value of 5.5 and then 0.2 mol of a 40% sodium peroxo disulfate solution are gradually added. The sulfobetaine disulfonate was obtained as the reaction product by about ⅔ and the sulfobetaine sulfonate by about ⅓.

Example 70

One proceeds in accordance with example 68 and admixes 0.2 mol methyltriallyl ammonium chloride solution, 0.7 mol sodium hydrogen sulfite solution and 2.8 g 37% hydrochloric acid into a homogeneous solution with a pH-value of 3.0 and then 0.3 mol of a 40% sodium peroxo disulfate solution is gradually added. The sulfobetaine disulfonate as well as the sulfobetaine trisulfonate are obtained as the reaction product at about equal portions in addition to a low amount of about 5% of the sulfobetaine sulfonate.

Example 71

This example should illustrate the suitability of an oxidation agent combination.

One proceeds in accordance with example 68 and produces a homogeneous initial solution with a pH-value of 4.5 from methyl triallyl ammonium chloride, sodium hydrogen sulfite and soda lye.

15 Mol-% of a 50% ammonium peroxo disulfate solution are at first added in about 1.5 minutes and subsequently 85 Mol-% 30% hydrogen peroxide at such a speed that the exothermic reaction could be controlled by boiling cooling, which required another 2 minutes. The product composition was the same as described in example 68. If the sulfonation products should be completely separated from their inorganic accompanying salts, one could proceed as follows.

After reducing the aforementioned recovered reaction solution into a dry state one reacts the received salt residue with the sufficient amount of concentrated hydrochloric acid and processes it well, filters off from the undissolved sodium salts and evaporates the hydrochloric acid of the sulfobetaine disulfonic acid under a reduced pressure. The sulfonic acid may be precipitated by adding ethanol to the remaining residue.

Example 72

Disodium-1-tetradecyl-1-(3'-sulfo)propyl-3,4-disulfomethyl-pyrrolidinium betaine
($R^1$=—$CH_2$—$CH_2$—$CH_2$—$SO_3^-$; $R^2$=$C_{14}H_{29}$;
$R^3$=—$CH_2$—$SO_3^-$; $R^4$=$R^5$=H in the general formula
I) from tetradecyl triallyl ammonium bromide One proceeds in accordance with one of the aforedescribed examples and reacts the combined solutions with a pH-value of 4.5 with 0.1 mol tetradecyl triallyl ammonium bromide and 0.3 mol sodium hydrogen sulfite into sodium peroxo disulfate. The neutralized clear reaction solution may be reduced to a dry state, if need be, so as to separate the sulfonation product from the inorganic salts with ethanol/water (2:1). The recrystallized product by the ethanol/water decomposed at a temperature above 284° C.

Example 73

Disodium-1-dodecyl/tetradecyl ammino carbonyl methyl-1-(3'-sulfo)propyl-3,4-disulfomethyl-pyrrolidinium betaine ($R^1$=—$CH_2$—$CH_2$—$CH_2$—$SO_3^-$;
$R^2$=$CH_2$—CO—NH—$C_{12}H_{25}/C_{14}H_{29}$;
$R^3$=$CH_2$—$SO_3^-$; $R^4$=$R^5$=H in the general formula I)

One proceeds in accordance with example 71 and reacts dodecyl/tetradecyl amino carbonyl methyl-triallyl ammonium chloride, which had been produced from triallyl amine, chlor acetic acid methyl ester and dodecyl/tetradecyl amine mixture (coconut amines, component ratio about 1:1), into sulfobetaine disulfonate mixture. After neutralisation with 33% soda lye and reducing to the dry state, the sulfobetaine disulfonate mixture was extracted with ethanol/water (weight ratio 2:1) and recrystallized. The reaction product decomposed at 234° C.

We claim:

1. 3-sulfinatomethyl- and 3-sulfonatomethyl-4-sulfomethyl-pyrrolidinium betaines of Formula Ia and Ib

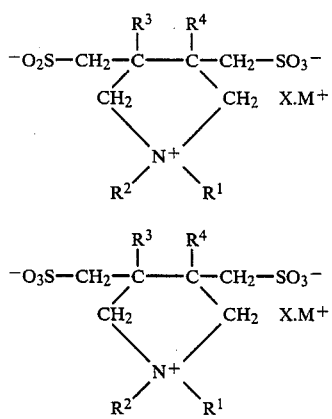

wherein
(A) $R^1$ is
 (a) hydrogen;
 (b) selected from the group consisting of
  (bi) unsubstituted $C_1$-$C_{22}$ alkyl,
  (bii) $CH_2$—CO—NH-alkyl, wherein alkyl is $CH_3$ to $C_{21}H_{43}$, and
  (biii) CH(CO—NH-alkyl)$_2$, wherein alkyl is $CH_3$ to $C_{21}H_{43}$;
 (c) 2-hydroxyethyl;
 (d) ($CH_2$—$CH_2$—O)$_n$H with n=1 to 10;
 (e) benzyl;
 (f) —$CH_2$—$CH_2$—$CH_2$—$SO_3^-$;
 (g)

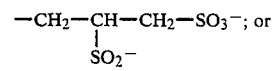

(h)

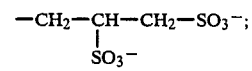

(B) $R^2$ is, independennt of $R^1$,
 (a) hydrogen;
 (b) selected from the group consisting of
  (bi) unsubstituted $C_1$-$C_{22}$ alkyl;
  (bii) $CH_2$—CO—NH-alkyl, wherein alkyl is $CH_3$ to $C_{21}H_{43}$; and
  (biii) CH(CO—NH—alkyl)$_2$, wherein alkyl is $CH_3$ to $C_{21}H_{43}$;
 (c) 2-hydroxyethyl or
 (d) ($CH_2$—$CH_2$—O)$_n$H with n=1 to 10;
(C) $R^1$ and $R^2$ form together with the nitrogen atom a substituted hetereocyclic ring with 4 carbon atoms of the structure

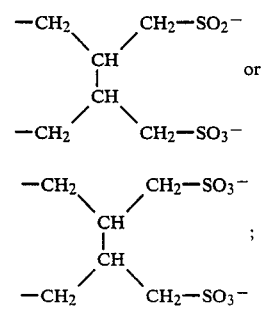

(D) $R^3$ and $R^4$ are hydrogen or methyl;
(E) M+ is selected from the group consisting of Na, K, NH$_4$ and H; and
(F) X represents a whole number from 1 to 3.

2. Process for the preparation of 3-sulfinatomethyl- and 3-sulfonatomethyl-4-sulfomethyl-pyrrolidinium betaines of Formula Ia and Ib according to claim 1 by reacting diallyl ammonium salts of Formula II

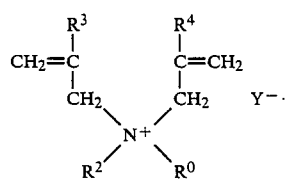

wherein
(A) $R^o$ is
 (a) hydrogen
 (b) selected from the group consisting of
  (bi) unsubstituted $C_1$-$C_{22}$ alkyl;
  (bii) $CH_2$—CO—NH-alkyl, wherein alkyl is $CH_3$ to $C_{21}H_{43}$, and
  (biii) CH(CO—NH-alkyl)$_2$, wherein alkyl is $CH_3$ to $C_{21}H_{43}$;

(c) 2-hydroxyethyl;
(d) $(CH_2-CH_2-O)_nH$ with n=1 to 10;
(e) benzyl;

(B) $R^2$ is, independent of $R^o$,
(a) hydrogen;
(b) selected from the group consisting of
(bi) unsubstituted $C_1$-$C_{22}$ alkyl,
(bii) $CH_2$—CO—NH-alkyl, wherein alkyl is $CH_3$ to $C_{21}H_{43}$, and
(biii) $CH(CO-NH-alkyl)_2$, wherein alkyl is $CH_3$ to $C_{21}H_{43}$;
(c) 2-hydroxyethyl;
(d) $(CH_2-CH_2O)_nH$ with n=1 to 10;

(C) $R^3$ and $R^4$ are hydrogen or methyl; and (D) $Y^-$ is selected from the group consisting of chloride, bromide, methosulfate and sulfate; or by reacting triallyl ammonium salts of Formula

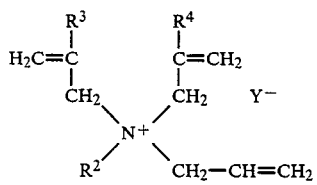

III wherein
(A) $R^2$ is
(a) hydrogen;
(b) selected from the group consisting of
(bi) unsubstituted $C_1$-$C_{22}$ alkyl,
(bii) $CH_2$—CO—NH-alkyl, wherein alkyl is $CH_3$ to $C_{21}H_{43}$, and
(biii) $CH(CO-NH-alkyl)_2$, wherein alkyl is $CH_3$ to $C_{21}H_{43}$;
(c) 2-hydroxyethyl;
(d) $(CH_2-CH_2O)_nH$ with n=1 to 10, or (e) allyl, (C) $R^3$ and $R^4$ are hydrogen or methyl; and (D) $Y^{31}$ is selected from the group consisting of chloride, bromide, methosulfate and sulfate; with hydrogen sulfite salts having the formula $MHSO_3$, wherein M is Na, K or $NH_4$, in the presence of peroxo disulfate salt having the formula $M_2S_2O_8$, wherein M is Na, K or $NH_4$, or in the presence of a mixture of a peroxo disulfate salt with other oxidation means having the formula $Cl_2$, MClO, $MClO_3$, $MBrO_3$, $H_2O_2$, or $O_2$, wherein M is Na, K or $NH_4$, in the pH-range from 1.5 to 6 and in an aqueous phase.

3. Process for the preparation of 3-sulfinatomethyl-4-sulfomethyl-pyrrolidinium betaines of Formula Ia according to claim 2:
(a) by reacting diallyl ammonium salts of Formula II with the double molar amount of hydrogen sulfite salts in the presence of a catalytic amount of peroxo disulfate salt in the pH-range of from 2 to 4;
(b) by reacting triallyl ammonium salts of Formula III with the triple molar amount of hydrogen sulfite salts in the presence of a catalytic amount of peroxo disulfate salt alone or in combination with a simultaneous or subsequent effect of oxygen in air in the pH-range from 2.5 to 6; or
(c) by reacting triallyl ammonium salts of Formula III with at least the quadruple molar amount of hydrogen sulfite salts in the presence of catalytic amount of a peroxo disulfate salt in the pH-range from 1.5 to 2.5.

4. The process of claim 3, wherein said reacting with the triple molar amount of hydrogen sulfite salts is effected with a pH-range between 4.0 and 5.5.

5. Process for the preparation of 3-sulfonatomethyl-4-sulfomethyl-pyrrolidinium betaines of Formula Ib according to claim 2:
(a) by reacting diallyl ammonium salts of Formula II with the double molar amount of hydrogen sulfite salts and one molar amount of peroxo disulfate salts alone or in combination with simultaneous presence of a mixture of peroxo disulfate salts with other oxidation means with a total of two oxidation equivalents in the pH-range from 2 to 4;
(b) by reacting triallyl ammonium salts of Formula III with the triple molar amount of hydrogen sulfite salts and one molar amount of peroxo disulfate salts alone or in combination with simultaneous presence of a mixture of peroxo disulfate salts with other oxidation means with a total of four oxidation equivalents in the pH-range from 1.5 to 2.5; or
(c) by reacting triallyl ammonium salts of Formula III with the quadruple molar amount of hydrogen sulfite salts and the double molar amount of peroxo disulfate salts or in combination with simultaneous presence of a mixture of peroxo disulfate salts with other oxidation means with a total of four oxidation equivalents in the pH-range from 1.5 to 2.5.

6. The process of claim 5, wherein said reacting with the triple molar amount of hydrogen sulfite salts is effected with a pH-range between 4.0 and 5.5.

7. Process for the preparation of 3-sulfinatomethyl- or 3-sulfonatomethyl-4-sulfomethyl-pyrrolidinium betaines of Formula Ia and Ib according to claim 2, wherein said oxidation means which are used in the mixture with peroxo disulfate salts are chlorine, chlorate, bromate, hydrogen peroxide or oxygen in air.

* * * * *